(12) United States Patent
Kim et al.

(10) Patent No.: US 7,175,840 B2
(45) Date of Patent: Feb. 13, 2007

(54) COMPOSITIONS FOR GENE THERAPY OF RHEUMATOID ARTHRITIS INCLUDING A GENE ENCODING AN ANTI-ANGIOGENIC PROTEIN OR PARTS THEREOF

(75) Inventors: Jong-Mook Kim, Seoul (KR); Seong-Hyun Ho, Seoul (KR); Eun-Jin Park, Seoul (KR); Sunyoung Kim, Seoul (KR)

(73) Assignee: Viromed Co., Ltd., Seoul (KR)

( * ) Notice: Subject to any disclaimer, the term of this patent is extended or adjusted under 35 U.S.C. 154(b) by 0 days.

(21) Appl. No.: 10/220,824

(22) PCT Filed: Jan. 3, 2002

(86) PCT No.: PCT/KR02/00001

§ 371 (c)(1),
(2), (4) Date: Aug. 30, 2002

(87) PCT Pub. No.: WO02/053191

PCT Pub. Date: Jul. 11, 2002

(65) Prior Publication Data

US 2005/0277603 A1    Dec. 15, 2005

(30) Foreign Application Priority Data

Jan. 5, 2001    (KR) .................... 10-2001-0000691

(51) Int. Cl.
| | |
|---|---|
| *A01N 63/00* | (2006.01) |
| *A01N 65/00* | (2006.01) |
| *A61K 48/00* | (2006.01) |
| *A01N 43/04* | (2006.01) |
| *A61K 31/715* | (2006.01) |
| *C12N 15/00* | (2006.01) |
| *C12N 15/09* | (2006.01) |
| *C12N 15/63* | (2006.01) |
| *C12N 15/70* | (2006.01) |
| *C12N 15/74* | (2006.01) |

(52) U.S. Cl. ............... 424/93.21; 424/93.2; 424/93.1; 514/44; 435/320.1

(58) Field of Classification Search ............... 514/44; 424/93.1; 536/23.4; 435/325
See application file for complete search history.

(56) References Cited

U.S. PATENT DOCUMENTS

| | | | | |
|---|---|---|---|---|
| 5,770,580 A | * | 6/1998 | Ledley et al. ............... 514/44 |
| 5,792,845 A | | 8/1998 | O'Reilly | |
| 5,837,682 A | * | 11/1998 | Folkman et al. ............... 514/12 |
| 5,858,355 A | * | 1/1999 | Glorioso et al. ............... 424/93.21 |
| 5,861,372 A | * | 1/1999 | Folkman et al. ............... 514/2 |
| 6,140,111 A | * | 10/2000 | Riviere et al. ............... 435/320.1 |
| 6,156,304 A | | 12/2000 | Glorioso et al. | |
| 6,190,907 B1 | | 2/2001 | Kim et al. | |
| 6,201,104 B1 | * | 3/2001 | MacDonald et al. ............... 530/327 |
| 2002/0115202 A1 | * | 8/2002 | Hallenbeck et al. ............... 435/320.1 |

FOREIGN PATENT DOCUMENTS

| | | |
|---|---|---|
| EP | 1 008 648 | 6/2000 |
| EP | 1 191 036 A2 | 3/2002 |
| EP | 1 197 550 A2 | 4/2002 |
| JP | 9-512173 A | 12/1997 |
| JP | 2001-254697 A | 9/2001 |
| JP | 2001-256030 A | 9/2001 |
| WO | WO 94/07524 A1 | 4/1994 |
| WO | WO 97/15666 A1 | 5/1997 |
| WO | WO 98/12338 A1 | 3/1998 |
| WO | WO 98/51791 | 11/1998 |
| WO | WO 99/65940 A1 | 12/1999 |
| WO | WO 00/00629 | 1/2000 |
| WO | WO 00/40737 | 7/2000 |
| WO | WO 01/73025 A2 | 10/2001 |
| WO | WO 02/45737 A2 | 6/2002 |

OTHER PUBLICATIONS

Dixelius, et al. (2000) Blood, 95(11): 3403-11.*
Pfeifer, et al. (2001) Fundamental Virology, 4th Ed., Lippincott, Williams, and Wilkins, New York, NY., p. 354.*
Robbins, et al. (2003) Gene Therapy, 10: 902-11.*
Griscelli, et al. (1998) Proc. Natl. Acad. Sci., USA., 95: 6367-72.*
Evans, et al. (1996) Hum. Gene Ther., 7: 1261-80.*
□□Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Yang, et al. (2002) Arthritis Res., 4(3): 215-19.*
Kim, et al. (2002) Arthritis & Rheumatism, 46(3): 793-801.*
Moore, et al. (2002) Mol. Biol. Cell., 13(12): 4388-400.*
Pawliuk, et al. (2002) Molec. Therap., 5(4): 345-51.*

(Continued)

*Primary Examiner*—Joseph Woitach
*Assistant Examiner*—Robert M. Kelly
(74) *Attorney, Agent, or Firm*—Sterne, Kessler, Goldstein & Fox P.L.L.C.

(57) ABSTRACT

The present invention relates to the compositions for a gene therapy of rheumatoid arthritis including a gene encoding an anti-angiogenic protein or parts thereof. More specifically, the present invention provides a gene therapy of rheumatoid arthritis by preparing a recombinant vector that expresses a gene encoding an anti-angiogenic protein such as angiostatin or parts thereof, and transplanting the recombinant vector or a cell that is transfected or transduced with the recombinant vector into the affected area of a patient, and also provides the compositions for the gene therapy. The compositions for the gene therapy according to the present invention can be used effectively for the treatment of rheumatoid arthritis, for which effective treating methods have not been developed until now, by providing the anti-angiogenic proteins into the knee of a patient continuously to prevent the synovial tissue hyperplasia and the resulting inflammation.

9 Claims, 6 Drawing Sheets

OTHER PUBLICATIONS

Yin, et al. (2002) Molec. Therap., 5(5): 547-54.*
Apparailly, et al. (2001) Arthritis & Rheumatism, 44: 1444-54.*
Shi, et al. (2002) Cancer Gene Therap., 9: 126-32).*
Sieminownow, et al. (2005) Transplantation Proceedings, 37: 201-04.*
Bakker, A.C., et al., "Prevention of Murine Collagen-induced Arthritis in the Knee and Ipsilateral Paw by Local Expression of Human Interleukin-1 Receptor Antagonist Protein in the Knee," *Arth. & Rheum.* 40:893-900, Lippincott, Williams & Wilkins (1997).
Byun, J., et al., "Analysis of the relative level of gene expression from different retroviral vectors used for gene therapy," *Gene Ther.* 3:780-788, Stockton Press (1996).
Griscelli, F., et al., "Angiostatin gene trasfer: Inhibition of tumor growth *in vivo* by blockage of endothelial cell proliferation associated with a mitosis arrest," *Proc. Natl. Acad. Sci. USA* 95:6367-6372, National Academy of Sciences (1998).
Hahn, W., et al., "Viral vector-mediated transduction of a modified thrombospondin-2 cDNA inhibits tumor growth and angiogenesis," *Gene Ther.* 11:739-745, Nature Publishing Company (May 2004).
Hong, Y., et al., "Construction of a high efficiency retroviral vector for gene therapy of Hunter's syndrome," *J. Gene Med.* 5:18-29, Wiley Interscience (Jan. 2003, published online Dec. 2002).
Kim, S.H., et al., "Construction of Retroviral Vectors with Improved Safety, Gene Expression, and Versatility," *J. Virol.* 72:994-1004, American Society for Microbiology (1998).
Kim, J.-M., et al., "Angiostatin Gene Transfer as an Effective Treatment Strategy in Murine Collagen-Induced Arthritis," *Arth. & Rheum.* 46:793-801, American College of Rheumatology (Mar. 2002).
Koch, A.E., "Angiogenesis: Implications for Rheumatoid Arthritis," *Arth. & Rheum.* 41:951-962, American College of Rheumatology (1998).
Lee, J.-T., et al., "Engineering the splice acceptor for improved gene expression and viral titer in an MLV-based retroviral vector," *Gene Ther.* 11:94-99, Nature Publishing Company (Jan. 2004).
Noguiez-Hellin, P., et al., "Plasmoviruses: Nonviral/viral vectors for gene therapy," *Proc. Natl. Acad. Sci. USA* 93:4175-4180, National Academy of Sciences (1996).
Nouvel, et al., "The spread if a replication-competent MuLV retroviral vector can be efficiently blocked by deletion variants," *Virol.* 204:180-189, Academic Press, Inc. (1994).
O'Reilly, M.S., et al., "Angiostatin: A Novel Angiogenesis Inhibitor That Mediates the Suppression of Metastases by a Lewis Lung Carcinoma," *Cell* 79:315-328, Cell Press (1994).
O'Reilly, M.S., et al., "Angiostatin induces and sustains dormancy of human primary tumors in mice," *Nat. Med.* 2:689-692, Nature Publishing Company (1996).
Otani, K., et al., "Suppression of Antigen-Induced Arthritis in Rabbits by Ex Vivo Gene Therapy," *J. Immunol.* 156:3558-3562, The American Association of Immunologists (1996).
Yu, S.S., et al., "High efficiency retroviral vectors that contain no viral coding sequences," *Gene Ther.* 7:797-804, Macmillan Publishers Ltd. (May 2000).
Chen, Q.-R., et al., "Liposomes Complexed to Plasmids Encoding Angiostatin and Endostatin Inhibit Breast Cancer in Nude Mice," *Cancer Res.* 59:3308-3312, The American Association for Cancer Research (1999).
Database Biosis, Accession No. PREV199799566462, Abstract of Wooley, P.H., et al., "A peptide sequence from platelet factor 4 (CT-112) is effective in the treatment of type II collagen induced arthritis in mice," *J. Rheumatol.* 24:890-898, The Journal of Rheumatology Publishing Company Limited (1997).
Davidoff, A.M., et al., "Retroviral Vector-Producer Cell Mediated Angiogenesis Inhibition Restricts Neuroblastoma Growth In Vivo," *Med. Pedriatr. Oncol.* 35:638-640, Wiley-Liss, Inc. (Dec. 2000).
Joki, T., et al., "Continuous Endostatin Release Using Alginate Polysine Polymer Encapsulated Producer Cells," *Proc. Am. Assoc. Cancer Res.* 41:524, Abstract No. 3342, American Association of Cancer Research (Mar. 2000).
Kim, J.-M., et al., "Angiostatin Gene Transfer as an Effective Treatment Strategy in Murine Collagen-Induced Arthritis," *Arthritis Rheumatism* 46:793-801, John Wiley & Sons, Inc. (Mar. 2002).
Oliver, S.J., et al., "Suppression of Collagen-Induced Arthritis Using an Angiogenesis Inhibitor, AGM-1470, and a Microtubule Stabilizer, Taxol," *Cell Immunol.* 157:291-299, Academic Press, Inc. (1994).
Tanaka, T., et al., "Viral vector-mediated transduction of a modified platelet factor 4 cDNA inhibits angiogenesis and tumor growth," *Nature Med.* 3:437-442, Nature Publishing Group (1997).
Tanaka, T., et al., "Retroviral and adenoviral mediated transduction of angiostatin cDNA inhibits angiogenesis and tumor growth," *Proc. Am. Assoc. Cancer Res.* 38:264, Abstract No. 1774, American Association of Cancer Research (1997).
Tanaka, T., et al., Inhibition of angiogenesis and tumor growth following retroviral-mediated transduction of a modified platelet factor 4 cDNA, *Proc. Am. Assoc. Cancer Res.* 37:54, Abstract No. 377, American Association of Cancer Research (1996).
Read, T.-A., et al., "Alginate encapsulated genetically engineered producer cells: A new treatment approach for malignant brain tumors," *Proc. Am. Assoc. Cancer Res.* 40:688, Abstract No. 4542, American Association of Cancer Research (1999).
Visted, T., et al., "Release of Angiostatin from Alginate-Encapsulated Producer Cells: A New Approach for the Treatment of Malignant Brain Tumors," *Proc. Am. Assoc. Cancer Res.* 41:258, Abstract No. 1641, American Association of Cancer Research (Mar. 2000).
Cao, Y., "Therapeutic potentials of angiostatin in the treatment of cancer," *Hematologica* 84:643-650, Ferrata Storti Foundation (1999).
Griffioen, A. W. and Molema, G., "Angiogenesis: Potentials for Pharmacologic Intervention in the Treatment of Cancer, Cardivascular Diseases and Chronic Inflammation,"*Pharmacol. Rev.* 52:237-268, American Society for Pharmacology and Experimental Therapeutics (Jun. 2000).
Woods, J.M., et al., "Adenoviral Interleukin (IL)-4 Gene Therapy Reduces Rat Adjuvant-Induced Arthritis (AIA) Bony Destruction, Synovial Leukocytosis, and Angiogenesis," *FASEB J.* 14:A651, Abstract No. 468.5 (Mar. 2000).
Woods, J.M., et al., "Interleukin-13 Adenoviral Gene Therapy Reduces Rat Adjuvant-Induced Arthritis (AIA) Associated Inflammation and Bony Destruction," *FASEB J.* 14:A651, Abstract No. 468.6 (Mar. 2000).

* cited by examiner

FIG. 1
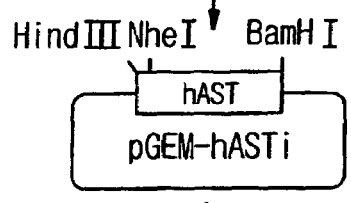
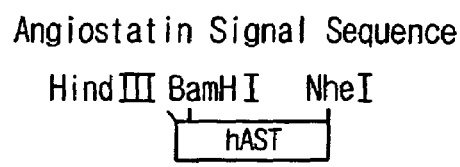
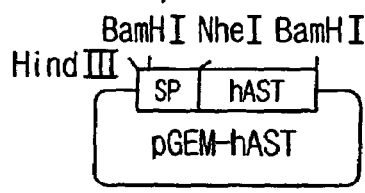
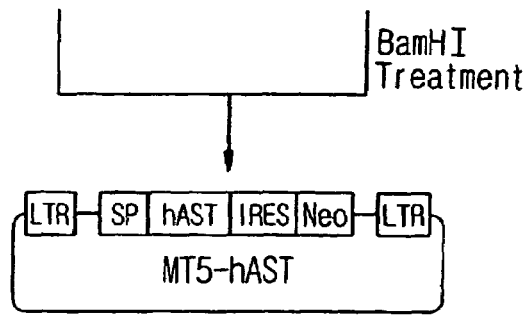

FIG. 2

Signal Peptide (Aminoacid 1-18)

SEQ ID No. 5  5' AGCTTGGATCCAAAATGGAACATAAGGAAGTGGTTCTTCTACTTCTTTTATTTCTGAAATCAGGTCAAG 3'
SEQ ID No. 6  3' ACCTAGGTTTTACCTTGTATTCCTTCACCAAGAAGATGAAGAAAATAAAGACTTTAGTCCAGTTCGATC 5'

↓ Hybridization

BamH I  Translation Start
HindIII
5' AGCTTGGATCCAAAATGGAACATAAGGAAGTGGTTCTTCTACTTCTTTTATTTCTGAAATCAGGTCAAG 3'
   ACCTAGGTTTTACCTTGTATTCCTTCACCAAGAAGATGAAGAAAATAAAGACTTTAGTCCAGTTCGATC
                                                                    NheI Aminoacid    M—E—H—K—E—V—V—L—L—L—L—F—L—K—S—G—Q FIG. 4
Control  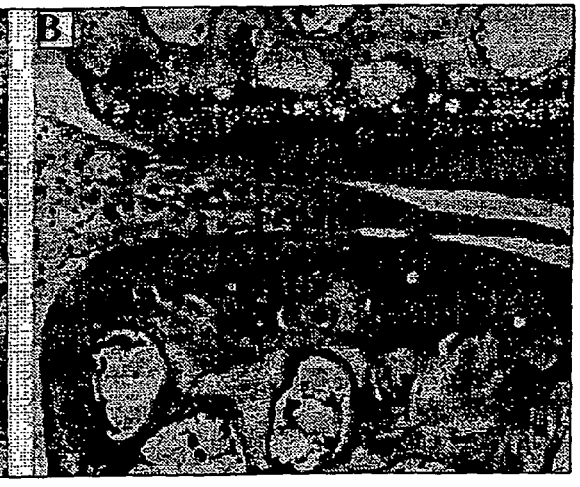 Angiostatin Control    Angiostatin

SEQUENCE LISTING

```
<160> NUMBER OF SEQ ID NOS: 16

<210> SEQ ID NO 1
<211> LENGTH: 2497
<212> TYPE: DNA
<213> ORGANISM: Homo sapiens
<220> FEATURE:
<221> NAME/KEY: CDS
<222> LOCATION: (50)..(2479)
<223> OTHER INFORMATION: gene encoding plasminogen with signal peptide

<400> SEQUENCE: 1
catcctggga ttgggaccca ctttctgggc actgctggcc agtcccaaa  atg gaa cat      58
                                                      Met Glu His
                                                        1 aag gaa gtg gtt ctt cta ctt ctt tta ttt ctg aaa tca ggt caa gga       106
Lys Glu Val Val Leu Leu Leu Leu Leu Phe Leu Lys Ser Gly Gln Gly
      5                  10                  15 gag cct ctg gat gac tat gtg aat acc cag ggg gct tca ctg ttc agt       154
Glu Pro Leu Asp Asp Tyr Val Asn Thr Gln Gly Ala Ser Leu Phe Ser
 20                  25                  30                  35 gtc act aag aag cag ctg gga gca gga agt ata gaa gaa tgt gca gca       202
Val Thr Lys Lys Gln Leu Gly Ala Gly Ser Ile Glu Glu Cys Ala Ala
                 40                  45                  50 aaa tgt gag gag gac gaa gaa ttc acc tgc agg gca ttc caa tat cac       250
Lys Cys Glu Glu Asp Glu Glu Phe Thr Cys Arg Ala Phe Gln Tyr His
             55                  60                  65 agt aaa gag caa caa tgt gtg ata atg gct gaa aac agg aag tcc tcc       298
Ser Lys Glu Gln Gln Cys Val Ile Met Ala Glu Asn Arg Lys Ser Ser
         70                  75                  80 ata atc att agg atg aga gat gta gtt tta ttt gaa aag aaa gtg tat       346
Ile Ile Ile Arg Met Arg Asp Val Val Leu Phe Glu Lys Lys Val Tyr
     85                  90                  95 ctc tca gag tgc aag act ggg aat gga aag aac tac aga ggg acg atg       394
Leu Ser Glu Cys Lys Thr Gly Asn Gly Lys Asn Tyr Arg Gly Thr Met
100                 105                 110                 115
```

```
tcc aaa aca aaa aat ggc atc acc tgt caa aaa tgg agt tcc act tct    442
Ser Lys Thr Lys Asn Gly Ile Thr Cys Gln Lys Trp Ser Ser Thr Ser
            120                 125                 130 ccc cac aga cct aga ttc tca cct gct aca cac ccc tca gag gga ctg    490
Pro His Arg Pro Arg Phe Ser Pro Ala Thr His Pro Ser Glu Gly Leu
        135                 140                 145 gag gag aac tac tgc agg aat cca gac aac gat ccg cag ggg ccc tgg    538
Glu Glu Asn Tyr Cys Arg Asn Pro Asp Asn Asp Pro Gln Gly Pro Trp
    150                 155                 160 tgc tat act act gat cca gaa aag aga tat gac tac tgc gac att ctt    586
Cys Tyr Thr Thr Asp Pro Glu Lys Arg Tyr Asp Tyr Cys Asp Ile Leu
165                 170                 175 gag tgt gaa gag gaa tgt atg cat tgc agt gga gaa aac tat gac ggc    634
Glu Cys Glu Glu Glu Cys Met His Cys Ser Gly Glu Asn Tyr Asp Gly
180                 185                 190                 195 aaa att tcc aag acc atg tct gga ctg gaa tgc cag gcc tgg gac tct    682
Lys Ile Ser Lys Thr Met Ser Gly Leu Glu Cys Gln Ala Trp Asp Ser
                200                 205                 210 cag agc cca cac gct cat gga tac att cct tcc aaa ttt cca aac aag    730
Gln Ser Pro His Ala His Gly Tyr Ile Pro Ser Lys Phe Pro Asn Lys
            215                 220                 225 aac ctg aag aag aat tac tgt cgt aac ccc gat agg gag ctg cgg cct    778
Asn Leu Lys Lys Asn Tyr Cys Arg Asn Pro Asp Arg Glu Leu Arg Pro
        230                 235                 240 tgg tgt ttc acc acc gac ccc aac aag cgc tgg gaa ctt tgt gac atc    826
Trp Cys Phe Thr Thr Asp Pro Asn Lys Arg Trp Glu Leu Cys Asp Ile
    245                 250                 255 ccc cgc tgc aca aca cct cca cca tct tct ggt ccc acc tac cag tgt    874
Pro Arg Cys Thr Thr Pro Pro Pro Ser Ser Gly Pro Thr Tyr Gln Cys
260                 265                 270                 275 ctg aag gga aca ggt gaa aac tat cgc ggg aat gtg gct gtt acc gtg    922
Leu Lys Gly Thr Gly Glu Asn Tyr Arg Gly Asn Val Ala Val Thr Val
                280                 285                 290 tcc ggg cac acc tgt cag cac tgg agt gca cag acc cct cac aca cat    970
Ser Gly His Thr Cys Gln His Trp Ser Ala Gln Thr Pro His Thr His
            295                 300                 305 aac agg aca cca gaa aac ttc ccc tgc aaa aat ttg gat gaa aac tac    1018
Asn Arg Thr Pro Glu Asn Phe Pro Cys Lys Asn Leu Asp Glu Asn Tyr
        310                 315                 320 tgc cgc aat cct gac gga aaa agg gcc cca tgg tgc cat aca acc aac    1066
Cys Arg Asn Pro Asp Gly Lys Arg Ala Pro Trp Cys His Thr Thr Asn
    325                 330                 335 agc caa gtg cgg tgg gag tac tgt aag ata ccg tcc tgt gac tcc tcc    1114
Ser Gln Val Arg Trp Glu Tyr Cys Lys Ile Pro Ser Cys Asp Ser Ser
340                 345                 350                 355 cca gta tcc acg gaa caa ttg gct ccc aca gca cca cct gag cta acc    1162
Pro Val Ser Thr Glu Gln Leu Ala Pro Thr Ala Pro Pro Glu Leu Thr
                360                 365                 370 cct gtg gtc cag gac tgc tac cat ggt gat gga cag agc tac cga ggc    1210
Pro Val Val Gln Asp Cys Tyr His Gly Asp Gly Gln Ser Tyr Arg Gly
            375                 380                 385 aca tcc tcc acc acc acc aca gga aag aag tgt cag tct tgg tca tct    1258
Thr Ser Ser Thr Thr Thr Thr Gly Lys Lys Cys Gln Ser Trp Ser Ser
        390                 395                 400 atg aca cca cac cgg cac cag aag acc cca gaa aac tac cca aat gct    1306
Met Thr Pro His Arg His Gln Lys Thr Pro Glu Asn Tyr Pro Asn Ala
405                 410                 415 ggc ctg aca atg aac tac tgc agg aat cca gat gcc gat aaa ggc ccc    1354
Gly Leu Thr Met Asn Tyr Cys Arg Asn Pro Asp Ala Asp Lys Gly Pro
```

-continued

| | | | | | | | | | | | | | | | | |
|---|---|---|---|---|---|---|---|---|---|---|---|---|---|---|---|---|
| | 420 | | | | 425 | | | | 430 | | | | 435 | | | |
| tgg | tgt | ttt | acc | aca | gac | ccc | agc | gtc | agg | tgg | gag | tac | tgc | aac | ctg | 1402 |
| Trp | Cys | Phe | Thr | Thr | Asp | Pro | Ser | Val | Arg | Trp | Glu | Tyr | Cys | Asn | Leu | |
| | | | | 440 | | | | | 445 | | | | | 450 | | |
| aaa | aaa | tgc | tca | gga | aca | gaa | gcg | agt | gtt | gta | gca | cct | ccg | cct | gtt | 1450 |
| Lys | Lys | Cys | Ser | Gly | Thr | Glu | Ala | Ser | Val | Val | Ala | Pro | Pro | Pro | Val | |
| | | | 455 | | | | | 460 | | | | | 465 | | | |
| gtc | ctg | ctt | cca | gat | gta | gag | act | cct | tcc | gaa | gaa | gac | tgt | atg | ttt | 1498 |
| Val | Leu | Leu | Pro | Asp | Val | Glu | Thr | Pro | Ser | Glu | Glu | Asp | Cys | Met | Phe | |
| | | | 470 | | | | | 475 | | | | | 480 | | | |
| ggg | aat | ggg | aaa | gga | tac | cga | ggc | aag | agg | gcg | acc | act | gtt | act | ggg | 1546 |
| Gly | Asn | Gly | Lys | Gly | Tyr | Arg | Gly | Lys | Arg | Ala | Thr | Thr | Val | Thr | Gly | |
| | | 485 | | | | | 490 | | | | | 495 | | | | |
| acg | cca | tgc | cag | gac | tgg | gct | gcc | cag | gag | ccc | cat | aga | cac | agc | att | 1594 |
| Thr | Pro | Cys | Gln | Asp | Trp | Ala | Ala | Gln | Glu | Pro | His | Arg | His | Ser | Ile | |
| 500 | | | | | 505 | | | | | 510 | | | | | 515 | |
| ttc | act | cca | gag | aca | aat | cca | cgg | gcg | ggt | ctg | gaa | aaa | aat | tac | tgc | 1642 |
| Phe | Thr | Pro | Glu | Thr | Asn | Pro | Arg | Ala | Gly | Leu | Glu | Lys | Asn | Tyr | Cys | |
| | | | | 520 | | | | | 525 | | | | | 530 | | |
| cgt | aac | cct | gat | ggt | gat | gta | ggt | ggt | ccc | tgg | tgc | tac | acg | aca | aat | 1690 |
| Arg | Asn | Pro | Asp | Gly | Asp | Val | Gly | Gly | Pro | Trp | Cys | Tyr | Thr | Thr | Asn | |
| | | | 535 | | | | | 540 | | | | | 545 | | | |
| cca | aga | aaa | ctt | tac | gac | tac | tgt | gat | gtc | cct | cag | tgt | gcg | gcc | cct | 1738 |
| Pro | Arg | Lys | Leu | Tyr | Asp | Tyr | Cys | Asp | Val | Pro | Gln | Cys | Ala | Ala | Pro | |
| | | | 550 | | | | | 555 | | | | | 560 | | | |
| tca | ttt | gat | tgt | ggg | aag | cct | caa | gtg | gag | ccg | aag | aaa | tgt | cct | gga | 1786 |
| Ser | Phe | Asp | Cys | Gly | Lys | Pro | Gln | Val | Glu | Pro | Lys | Lys | Cys | Pro | Gly | |
| | 565 | | | | | 570 | | | | | 575 | | | | | |
| agg | gtt | gta | ggg | ggg | tgt | gtg | gcc | cac | cca | cat | tcc | tgg | ccc | tgg | caa | 1834 |
| Arg | Val | Val | Gly | Gly | Cys | Val | Ala | His | Pro | His | Ser | Trp | Pro | Trp | Gln | |
| 580 | | | | | 585 | | | | | 590 | | | | | 595 | |
| gtc | agt | ctt | aga | aca | agg | ttt | gga | atg | cac | ttc | tgt | gga | ggc | acc | ttg | 1882 |
| Val | Ser | Leu | Arg | Thr | Arg | Phe | Gly | Met | His | Phe | Cys | Gly | Gly | Thr | Leu | |
| | | | | 600 | | | | | 605 | | | | | 610 | | |
| ata | tcc | cca | gag | tgg | gtg | ttg | act | gct | gcc | cac | tgc | ttg | gag | aag | tcc | 1930 |
| Ile | Ser | Pro | Glu | Trp | Val | Leu | Thr | Ala | Ala | His | Cys | Leu | Glu | Lys | Ser | |
| | | | 615 | | | | | 620 | | | | | 625 | | | |
| cca | agg | cct | tca | tcc | tac | aag | gtc | atc | ctg | ggt | gca | cac | caa | gaa | gtg | 1978 |
| Pro | Arg | Pro | Ser | Ser | Tyr | Lys | Val | Ile | Leu | Gly | Ala | His | Gln | Glu | Val | |
| | | 630 | | | | | 635 | | | | | 640 | | | | |
| aat | ctc | gaa | ccg | cat | gtt | cag | gaa | ata | gaa | gtg | tct | agg | ctg | ttc | ttg | 2026 |
| Asn | Leu | Glu | Pro | His | Val | Gln | Glu | Ile | Glu | Val | Ser | Arg | Leu | Phe | Leu | |
| | 645 | | | | | 650 | | | | | 655 | | | | | |
| gag | ccc | aca | cga | aaa | gat | att | gcc | ttg | cta | aag | cta | agc | agt | cct | gcc | 2074 |
| Glu | Pro | Thr | Arg | Lys | Asp | Ile | Ala | Leu | Leu | Lys | Leu | Ser | Ser | Pro | Ala | |
| 660 | | | | | 665 | | | | | 670 | | | | | 675 | |
| gtc | atc | act | gac | aaa | gta | atc | cca | gct | tgt | ctg | cca | tcc | cca | aat | tat | 2122 |
| Val | Ile | Thr | Asp | Lys | Val | Ile | Pro | Ala | Cys | Leu | Pro | Ser | Pro | Asn | Tyr | |
| | | | | 680 | | | | | 685 | | | | | 690 | | |
| gtg | gtc | gct | gac | cgg | acc | gaa | tgt | ttc | gtc | act | ggc | tgg | gga | gaa | acc | 2170 |
| Val | Val | Ala | Asp | Arg | Thr | Glu | Cys | Phe | Val | Thr | Gly | Trp | Gly | Glu | Thr | |
| | | | 695 | | | | | 700 | | | | | 705 | | | |
| caa | ggt | act | ttt | gga | gct | ggc | ctt | ctc | aag | gaa | gcc | cag | ctc | cct | gtg | 2218 |
| Gln | Gly | Thr | Phe | Gly | Ala | Gly | Leu | Leu | Lys | Glu | Ala | Gln | Leu | Pro | Val | |
| | | 710 | | | | | 715 | | | | | 720 | | | | |
| att | gag | aat | aaa | gtg | tgc | aat | cgc | tat | gag | ttt | ctg | aat | gga | aga | gtc | 2266 |
| Ile | Glu | Asn | Lys | Val | Cys | Asn | Arg | Tyr | Glu | Phe | Leu | Asn | Gly | Arg | Val | |
| | 725 | | | | | 730 | | | | | 735 | | | | | |
| caa | tcc | acc | gaa | ctc | tgt | gct | ggg | cat | ttg | gcc | gga | ggc | act | gac | agt | 2314 |

```
Gln Ser Thr Glu Leu Cys Ala Gly His Leu Ala Gly Gly Thr Asp Ser
740                 745                 750                 755 tgc cag ggt gac agt gga ggt cct ctg gtt tgc ttc gag aag gac aaa    2362
Cys Gln Gly Asp Ser Gly Gly Pro Leu Val Cys Phe Glu Lys Asp Lys
                760                 765                 770 tac att tta caa gga gtc act tct tgg ggt ctt ggc tgt gca cgc ccc    2410
Tyr Ile Leu Gln Gly Val Thr Ser Trp Gly Leu Gly Cys Ala Arg Pro
                775                 780                 785 aat aag cct ggt gtc tat gtt cgt gtt tca agg ttt gtt act tgg att    2458
Asn Lys Pro Gly Val Tyr Val Arg Val Ser Arg Phe Val Thr Trp Ile
                790                 795                 800 gag gga gtg atg aga aat aat     t aattggacgg gagacag               2497
Glu Gly Val Met Arg Asn Asn
805                 810

<210> SEQ ID NO 2
<211> LENGTH: 810
<212> TYPE: PRT
<213> ORGANISM: Homo sapiens

<400> SEQUENCE: 2

Met Glu His Lys Glu Val Val Leu Leu Leu Leu Phe Leu Lys Ser
  1               5                  10                  15

Gly Gln Gly Glu Pro Leu Asp Asp Tyr Val Asn Thr Gln Gly Ala Ser
                 20                  25                  30

Leu Phe Ser Val Thr Lys Lys Gln Leu Gly Ala Gly Ser Ile Glu Glu
             35                  40                  45

Cys Ala Ala Lys Cys Glu Glu Asp Glu Glu Phe Thr Cys Arg Ala Phe
         50                  55                  60

Gln Tyr His Ser Lys Glu Gln Gln Cys Val Ile Met Ala Glu Asn Arg
 65                  70                  75                  80

Lys Ser Ser Ile Ile Ile Arg Met Arg Asp Val Val Leu Phe Glu Lys
                 85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
        130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
        210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
```

-continued

```
                275                 280                 285
Val Thr Val Ser Gly His Thr Cys Gln His Trp Ser Ala Gln Thr Pro
290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
                340                 345                 350
Asp Ser Ser Pro Val Ser Thr Glu Gln Leu Ala Pro Thr Ala Pro Pro
                355                 360                 365
Glu Leu Thr Pro Val Val Gln Asp Cys Tyr His Gly Asp Gly Gln Ser
370                 375                 380
Tyr Arg Gly Thr Ser Ser Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
                420                 425                 430
Lys Gly Pro Trp Cys Phe Thr Thr Asp Pro Ser Val Arg Trp Glu Tyr
                435                 440                 445
Cys Asn Leu Lys Lys Cys Ser Gly Thr Glu Ala Ser Val Val Ala Pro
                450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
                500                 505                 510
His Ser Ile Phe Thr Pro Glu Thr Asn Pro Arg Ala Gly Leu Glu Lys
                515                 520                 525
Asn Tyr Cys Arg Asn Pro Asp Gly Asp Val Gly Gly Pro Trp Cys Tyr
                530                 535                 540
Thr Thr Asn Pro Arg Lys Leu Tyr Asp Tyr Cys Asp Val Pro Gln Cys
545                 550                 555                 560
Ala Ala Pro Ser Phe Asp Cys Gly Lys Pro Gln Val Glu Pro Lys Lys
                565                 570                 575
Cys Pro Gly Arg Val Val Gly Gly Cys Val Ala His Pro His Ser Trp
                580                 585                 590
Pro Trp Gln Val Ser Leu Arg Thr Arg Phe Gly Met His Phe Cys Gly
                595                 600                 605
Gly Thr Leu Ile Ser Pro Glu Trp Val Leu Thr Ala Ala His Cys Leu
                610                 615                 620
Glu Lys Ser Pro Arg Pro Ser Ser Tyr Lys Val Ile Leu Gly Ala His
625                 630                 635                 640
Gln Glu Val Asn Leu Glu Pro His Val Gln Glu Ile Glu Val Ser Arg
                645                 650                 655
Leu Phe Leu Glu Pro Thr Arg Lys Asp Ile Ala Leu Leu Lys Leu Ser
                660                 665                 670
Ser Pro Ala Val Ile Thr Asp Lys Val Ile Pro Ala Cys Leu Pro Ser
                675                 680                 685
Pro Asn Tyr Val Val Ala Asp Arg Thr Glu Cys Phe Val Thr Gly Trp
                690                 695                 700
```

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 3
<211> LENGTH: 51
<212> TYPE: DNA
<213> ORGANISM: Artificial Sequence
<220> FEATURE:
<223> OTHER INFORMATION: hAST 5'primer for PCR of human angiostatin gene

<400> SEQUENCE: 3
aagcttgcta gcttatttga aaagaaagtg tatctctcag agtgcaagac t         51

<210> SEQ ID NO 4
<211> LENGTH: 39
<212> TYPE: DNA
<213> ORGANISM: Artificial Sequence
<220> FEATURE:
<223> OTHER INFORMATION: hAST 3'primer for PCR of human angiostatin gene

<400> SEQUENCE: 4
ggatcctcat taaggtggtg ctgtgggagc caattgttc                       39

<210> SEQ ID NO 5
<211> LENGTH: 69
<212> TYPE: DNA
<213> ORGANISM: Artificial Sequence
<220> FEATURE:
<223> OTHER INFORMATION: hASTsignal5

<400> SEQUENCE: 5
agcttggatc caaaatggaa cataaggaag tggttcttct acttctttta tttctgaaat    60
caggtcaag                                                           69

<210> SEQ ID NO 6
<211> LENGTH: 69
<212> TYPE: DNA
<213> ORGANISM: Artificial Sequence
<220> FEATURE:
<223> OTHER INFORMATION: hASTsignal3

<400> SEQUENCE: 6
ctagcttgac ctgatttcag aaataaaaga agtagaagaa ccacttcctt atgttccatt    60
ttggatcca                                                           69

<210> SEQ ID NO 7
<211> LENGTH: 4551
<212> TYPE: DNA
<213> ORGANISM: Homo sapiens -continued

```
<220> FEATURE:
<221> NAME/KEY: CDS
<222> LOCATION: (1)..(4548)

<400> SEQUENCE: 7 atg gct ccc tac ccc tgt ggc tgc cac atc ctg ctg ctg ctc ttc tgc      48
Met Ala Pro Tyr Pro Cys Gly Cys His Ile Leu Leu Leu Leu Phe Cys
 1               5                  10                  15 tgc ctg gcg gct gcc cgg gcc aac ctg ctg aac ctg aac tgg ctt tgg      96
Cys Leu Ala Ala Ala Arg Ala Asn Leu Leu Asn Leu Asn Trp Leu Trp
             20                  25                  30 ttc aat aat gag gac acc agc cac gca gct acc acg atc cct gag ccc      144
Phe Asn Asn Glu Asp Thr Ser His Ala Ala Thr Thr Ile Pro Glu Pro
         35                  40                  45 cag ggg ccc ctg cct gtg cag ccc aca gca gat acc acc aca cac gtg      192
Gln Gly Pro Leu Pro Val Gln Pro Thr Ala Asp Thr Thr Thr His Val
     50                  55                  60 acc ccc cgg aat ggt tcc aca gag cca gcg aca gcc cct ggc agc cct      240
Thr Pro Arg Asn Gly Ser Thr Glu Pro Ala Thr Ala Pro Gly Ser Pro
 65                  70                  75                  80 gag cca ccc tca gag ctg ctg gaa gat ggc cag gac acc ccc act tct      288
Glu Pro Pro Ser Glu Leu Leu Glu Asp Gly Gln Asp Thr Pro Thr Ser
                 85                  90                  95 gcc gag agc ccg gac gcg cca gag gag aac att gcc ggt gtc gga gcc      336
Ala Glu Ser Pro Asp Ala Pro Glu Glu Asn Ile Ala Gly Val Gly Ala
            100                 105                 110 gag atc ctg aac gtg gcc aaa ggc atc cgg agc ttc gtc cag ctg tgg      384
Glu Ile Leu Asn Val Ala Lys Gly Ile Arg Ser Phe Val Gln Leu Trp
        115                 120                 125 aat gac act gtc ccc act gag agc ttg gcc agg gcg gaa acc ctg gtc      432
Asn Asp Thr Val Pro Thr Glu Ser Leu Ala Arg Ala Glu Thr Leu Val
    130                 135                 140 ctg gag act cct gtg ggc ccc ctt gcc ctc gct ggg cct tcc agc acc      480
Leu Glu Thr Pro Val Gly Pro Leu Ala Leu Ala Gly Pro Ser Ser Thr
145                 150                 155                 160 ccc cag gag aat ggg acc act ctc tgg ccc agc cgt ggc att cct agc      528
Pro Gln Glu Asn Gly Thr Thr Leu Trp Pro Ser Arg Gly Ile Pro Ser
                165                 170                 175 tct ccg ggc gcc cac aca acc gag gct ggc acc ttg cct gca ccc acc      576
Ser Pro Gly Ala His Thr Thr Glu Ala Gly Thr Leu Pro Ala Pro Thr
            180                 185                 190 cca tcg cct ccg tcc ctg ggc agg ccc tgg gca cca ctc acg ggg ccc      624
Pro Ser Pro Pro Ser Leu Gly Arg Pro Trp Ala Pro Leu Thr Gly Pro
        195                 200                 205 tca gtg cca cca cca tct tca gag cgc atc agc gag gag gtg ggg ctg      672
Ser Val Pro Pro Pro Ser Ser Glu Arg Ile Ser Glu Glu Val Gly Leu
    210                 215                 220 ctg cag ctc ctt ggg gac ccc ccg ccc cag cag gtc acc cag acg gat      720
Leu Gln Leu Leu Gly Asp Pro Pro Pro Gln Gln Val Thr Gln Thr Asp
225                 230                 235                 240 gac ccc gac gtc ggg ctg gcc tac gtc ttt ggg cca gat gcc aac agt      768
Asp Pro Asp Val Gly Leu Ala Tyr Val Phe Gly Pro Asp Ala Asn Ser
                245                 250                 255 ggc caa gtg gcc cgg tac cac ttc ccc agc ctc ttc cgt gac ttc      816
Gly Gln Val Ala Arg Tyr His Phe Pro Ser Leu Phe Arg Asp Phe
            260                 265                 270 tca ctg ctg ttc cac atc cgg cca gcc aca gag ggc cca ggg gtg ctg      864
Ser Leu Leu Phe His Ile Arg Pro Ala Thr Glu Gly Pro Gly Val Leu
        275                 280                 285 ttc gcc atc acg gac tcg gcg cag gcc atg gtc ttg ctg ggc gtg aag      912
```

|  |  |  |  |  |  |  |  |  |  |  |  |  |
|---|---|---|---|---|---|---|---|---|---|---|---|---|
| Phe | Ala | Ile | Thr | Asp | Ser | Ala | Gln | Ala | Met | Val | Leu | Leu | Gly | Val | Lys |
|  | 290 |  |  |  | 295 |  |  |  | 300 |  |  |  |  |  |  |

```
ctc tct ggg gtg cag gac ggg cac cag gac atc tcc ctg ctc tac aca        60
Leu Ser Gly Val Gln Asp Gly His Gln Asp Ile Ser Leu Leu Tyr Thr
305             310             315             320 gaa cct ggt gca ggc cag acc cac aca gcc gcc agc ttc cgg ctc ccc      1008
Glu Pro Gly Ala Gly Gln Thr His Thr Ala Ala Ser Phe Arg Leu Pro
            325             330             335 gcc ttc gtc ggc cag tgg aca cac tta gcc ctc agt gtg gca ggt ggc      1056
Ala Phe Val Gly Gln Trp Thr His Leu Ala Leu Ser Val Ala Gly Gly
        340             345             350 ttt gtg gcc ctc tac gtg gac tgt gag gag ttc cag aga atg ccg ctt      1104
Phe Val Ala Leu Tyr Val Asp Cys Glu Glu Phe Gln Arg Met Pro Leu
    355             360             365 gct cgg tcc tca cgg ggc ctg gag ctg gag cct ggc gcc ggg ctc ttc      1152
Ala Arg Ser Ser Arg Gly Leu Glu Leu Glu Pro Gly Ala Gly Leu Phe
370             375             380 gtg gct cag gcg ggg gga gcg gac cct gac aag ttc cag ggg gtg atc      1200
Val Ala Gln Ala Gly Gly Ala Asp Pro Asp Lys Phe Gln Gly Val Ile
385             390             395             400 gct gag ctg aag gtg cgc agg gac ccc cag gtg agc ccc atg cac tgc      1248
Ala Glu Leu Lys Val Arg Arg Asp Pro Gln Val Ser Pro Met His Cys
        405             410             415 ctg gac gag gaa ggc gat gac tca gat ggg gca ttc gga gac tct ggc      1296
Leu Asp Glu Glu Gly Asp Asp Ser Asp Gly Ala Phe Gly Asp Ser Gly
            420             425             430 agc ggg ctc ggg gac gcc cgg gag ctt ctc agg gag gag acg ggc gcg      1344
Ser Gly Leu Gly Asp Ala Arg Glu Leu Leu Arg Glu Glu Thr Gly Ala
        435             440             445 gcc cta aaa ccc agg ctc ccc gcg cca ccc ccc gtc acc acg cca ccc      1392
Ala Leu Lys Pro Arg Leu Pro Ala Pro Pro Pro Val Thr Thr Pro Pro
450             455             460 ttg gct gga ggc agc agc acg gaa gat tcc aga agt gaa gaa gtc gag      1440
Leu Ala Gly Gly Ser Ser Thr Glu Asp Ser Arg Ser Glu Glu Val Glu
465             470             475             480 gag cag acc acg gtg gct tcg tta gga gct cag aca ctt cct ggc tca      1488
Glu Gln Thr Thr Val Ala Ser Leu Gly Ala Gln Thr Leu Pro Gly Ser
            485             490             495 gat tct gtc tcc acg tgg gac ggg agt gtc cgg acc cct ggg ggc cgc      1536
Asp Ser Val Ser Thr Trp Asp Gly Ser Val Arg Thr Pro Gly Gly Arg
        500             505             510 gtg aaa gag ggc ggc ctg aag ggg cag aaa ggg gag cca ggt gtt ccg      1584
Val Lys Glu Gly Gly Leu Lys Gly Gln Lys Gly Glu Pro Gly Val Pro
    515             520             525 ggc cca cct ggc cgg gca ggc ccc cca gga tcc cca tgc cta cct ggt      1632
Gly Pro Pro Gly Arg Ala Gly Pro Pro Gly Ser Pro Cys Leu Pro Gly
530             535             540 ccc ccg ggt ctc ccg tgc cca gtg agt ccc ctg ggt cct gca ggc cca      1680
Pro Pro Gly Leu Pro Cys Pro Val Ser Pro Leu Gly Pro Ala Gly Pro
545             550             555             560 gcg ttg caa act gtc ccc gga cca caa gga ccc cca ggg cct ccg ggg      1728
Ala Leu Gln Thr Val Pro Gly Pro Gln Gly Pro Pro Gly Pro Pro Gly
            565             570             575 agg gac ggc acc cct gga agg gac ggc gag ccg ggc gac ccc ggt gaa      1776
Arg Asp Gly Thr Pro Gly Arg Asp Gly Glu Pro Gly Asp Pro Gly Glu
        580             585             590 gac gga aag ccg ggc gac acc ggg cca caa ggc ttc cct ggg act cca      1824
Asp Gly Lys Pro Gly Asp Thr Gly Pro Gln Gly Phe Pro Gly Thr Pro
    595             600             605
```

-continued

| | | |
|---|---|---|
| ggg gat gta ggt ccc aag gga gac aag gga gac cct ggg gtt gga gag<br>Gly Asp Val Gly Pro Lys Gly Asp Lys Gly Asp Pro Gly Val Gly Glu<br>610                           615                     620 | 1872 |
| aga ggg ccc cca gga ccc caa ggg cct cca ggg ccc cca gga ccc tcc<br>Arg Gly Pro Pro Gly Pro Gln Gly Pro Pro Gly Pro Pro Gly Pro Ser<br>625                     630                   635                   640 | 1920 |
| ttc aga cac gac aag ctg acc ttc att gac atg gag gga tct ggc ttt<br>Phe Arg His Asp Lys Leu Thr Phe Ile Asp Met Glu Gly Ser Gly Phe<br>                    645                   650                   655 | 1968 |
| ggg ggc gat ctg gag gcc ctg cgg ggt cct cga ggc ttc cct gga cct<br>Gly Gly Asp Leu Glu Ala Leu Arg Gly Pro Arg Gly Phe Pro Gly Pro<br>                660                   665                   670 | 2016 |
| ccc gga ccc ccc ggt gtc cca ggc ctg ccc ggc gag cca ggc cgc ttt<br>Pro Gly Pro Pro Gly Val Pro Gly Leu Pro Gly Glu Pro Gly Arg Phe<br>675                     680                   685 | 2064 |
| ggg gtg aac agc tcc gac gtc cca gga ccc gcc ggc ctt cct ggt gtg<br>Gly Val Asn Ser Ser Asp Val Pro Gly Pro Ala Gly Leu Pro Gly Val<br>690                     695                   700 | 2112 |
| cct ggg cgc gag ggt ccc ccc ggg ttt cct ggc ctc ccg gga ccc cca<br>Pro Gly Arg Glu Gly Pro Pro Gly Phe Pro Gly Leu Pro Gly Pro Pro<br>705                     710                   715                   720 | 2160 |
| ggc cct ccg gga aga gag ggg ccc cca gga agg act ggg cag aaa ggc<br>Gly Pro Pro Gly Arg Glu Gly Pro Pro Gly Arg Thr Gly Gln Lys Gly<br>                    725                   730                   735 | 2208 |
| agc ctg ggt gaa gca ggc gcc cca gga cat aag ggg agc aag gga gcc<br>Ser Leu Gly Glu Ala Gly Ala Pro Gly His Lys Gly Ser Lys Gly Ala<br>                740                   745                   750 | 2256 |
| ccc ggt cct gct ggt gct cgt ggg gag agc ggc ctg gca gga gcc ccc<br>Pro Gly Pro Ala Gly Ala Arg Gly Glu Ser Gly Leu Ala Gly Ala Pro<br>755                     760                   765 | 2304 |
| gga cct gct gga cca cca ggc ccc cct ggg ccc cct ggg ccc cca gga<br>Gly Pro Ala Gly Pro Pro Gly Pro Pro Gly Pro Pro Gly Pro Pro Gly<br>770                     775                   780 | 2352 |
| cca gga ctc ccc gct gga ttt gat gac atg gaa ggc tcc ggg ggg ccc<br>Pro Gly Leu Pro Ala Gly Phe Asp Asp Met Glu Gly Ser Gly Gly Pro<br>785                     790                   795                   800 | 2400 |
| ttc tgg tca aca gcc cga agc gct gat ggg cca cag gga cct ccc ggc<br>Phe Trp Ser Thr Ala Arg Ser Ala Asp Gly Pro Gln Gly Pro Pro Gly<br>                805                   810                   815 | 2448 |
| ctg ccg gga ctt aag ggg gat cct ggc gtg cct ggg ctg ccg ggg gcg<br>Leu Pro Gly Leu Lys Gly Asp Pro Gly Val Pro Gly Leu Pro Gly Ala<br>                820                   825                   830 | 2496 |
| aag gga gaa gtt gga gca gat gga atc ccc ggg ttc ccc ggc ctc cct<br>Lys Gly Glu Val Gly Ala Asp Gly Ile Pro Gly Phe Pro Gly Leu Pro<br>835                     840                   845 | 2544 |
| ggc aga gag ggc att gct ggg ccc cag ggg cca aag gga gac aga ggc<br>Gly Arg Glu Gly Ile Ala Gly Pro Gln Gly Pro Lys Gly Asp Arg Gly<br>850                     855                   860 | 2592 |
| agc cgg gga gaa aag gga gat cca ggg aag gac gga gtc ggg cag ccg<br>Ser Arg Gly Glu Lys Gly Asp Pro Gly Lys Asp Gly Val Gly Gln Pro<br>865                     870                   875                   880 | 2640 |
| ggc ctc cct ggc ccc ccc gga ccc ccg gga cct gtg gtc tac gtg tcg<br>Gly Leu Pro Gly Pro Pro Gly Pro Pro Gly Pro Val Val Tyr Val Ser<br>                885                   890                   895 | 2688 |
| gag cag gac gga tcc gtc ctg agc gtg ccg gga cct gag ggc cgg ccg<br>Glu Gln Asp Gly Ser Val Leu Ser Val Pro Gly Pro Glu Gly Arg Pro<br>                900                   905                   910 | 2736 |
| ggt ttc gca ggc ttt ccc gga cct gca gga ccc aag ggc aac ctg ggc<br>Gly Phe Ala Gly Phe Pro Gly Pro Ala Gly Pro Lys Gly Asn Leu Gly<br>915                     920                   925 | 2784 |

-continued

| | |
|---|---|
| tct aag ggc gaa cga ggc tcc ccg gga ccc aag ggt gag aag ggt gaa<br>Ser Lys Gly Glu Arg Gly Ser Pro Gly Pro Lys Gly Glu Lys Gly Glu<br>930                935              940 | 2832 |
| ccg ggc agc atc ttc agc ccc gac ggc ggt gcc ctg ggc cct gcc cag<br>Pro Gly Ser Ile Phe Ser Pro Asp Gly Gly Ala Leu Gly Pro Ala Gln<br>945                950              955              960 | 2880 |
| aaa gga gcc aag gga gag ccg ggc ttc cga gga ccc ccg ggt cca tac<br>Lys Gly Ala Lys Gly Glu Pro Gly Phe Arg Gly Pro Pro Gly Pro Tyr<br>965                970              975 | 2928 |
| gga cgg ccg ggg tac aag gga gag att ggc ttt cct gga cgg ccg ggt<br>Gly Arg Pro Gly Tyr Lys Gly Glu Ile Gly Phe Pro Gly Arg Pro Gly<br>980                985              990 | 2976 |
| cgc ccc ggg atg aac gga ttg aaa gga gag aaa ggg gag ccg gga gat<br>Arg Pro Gly Met Asn Gly Leu Lys Gly Glu Lys Gly Glu Pro Gly Asp<br>995                1000            1005 | 3024 |
| gcc agc ctt gga ttt ggc atg agg gga atg ccc ggc ccc cca gga cct<br>Ala Ser Leu Gly Phe Gly Met Arg Gly Met Pro Gly Pro Pro Gly Pro<br>1010            1015            1020 | 3072 |
| cca ggg ccc cca ggc cct cca ggg act cct gtt tac gac agc aat gtg<br>Pro Gly Pro Pro Gly Pro Pro Gly Thr Pro Val Tyr Asp Ser Asn Val<br>1025            1030            1035           1040 | 3120 |
| ttt gct gag tcc agc cgc ccc ggg cct cca gga ttg cca ggg aat cag<br>Phe Ala Glu Ser Ser Arg Pro Gly Pro Pro Gly Leu Pro Gly Asn Gln<br>1045            1050            1055 | 3168 |
| ggc cct cca gga ccc aag ggc gcc aaa gga gaa gtg ggc ccc ccc gga<br>Gly Pro Pro Gly Pro Lys Gly Ala Lys Gly Glu Val Gly Pro Pro Gly<br>1060            1065            1070 | 3216 |
| cca cca ggg cag ttt ccg ttt gac ttt ctt cag ttg gag gct gaa atg<br>Pro Pro Gly Gln Phe Pro Phe Asp Phe Leu Gln Leu Glu Ala Glu Met<br>1075            1080            1085 | 3264 |
| aag ggg gag aag gga gac cga ggt gat gca gga cag aaa ggc gaa agg<br>Lys Gly Glu Lys Gly Asp Arg Gly Asp Ala Gly Gln Lys Gly Glu Arg<br>1090            1095            1100 | 3312 |
| ggg gag ccc ggg ggc ggc ggt ttc ttc ggc tcc agc ctg ccc ggc ccc<br>Gly Glu Pro Gly Gly Gly Gly Phe Phe Gly Ser Ser Leu Pro Gly Pro<br>1105            1110            1115           1120 | 3360 |
| ccc ggc ccc cca ggc cca cgt ggc tac cct ggg att cca ggt ccc aag<br>Pro Gly Pro Pro Gly Pro Arg Gly Tyr Pro Gly Ile Pro Gly Pro Lys<br>1125            1130            1135 | 3408 |
| gga gag agc atc cgg ggc cag ccc ggc cca cct gga cct cag gga ccc<br>Gly Glu Ser Ile Arg Gly Gln Pro Gly Pro Pro Gly Pro Gln Gly Pro<br>1140            1145            1150 | 3456 |
| ccc ggc atc ggc tac gag ggg cgc cag ggc cct ccc ggc ccc cca ggc<br>Pro Gly Ile Gly Tyr Glu Gly Arg Gln Gly Pro Pro Gly Pro Pro Gly<br>1155            1160            1165 | 3504 |
| ccc cca ggg ccc cct tca ttt cct ggc cct cac agg cag act atc agc<br>Pro Pro Gly Pro Pro Ser Phe Pro Gly Pro His Arg Gln Thr Ile Ser<br>1170            1175            1180 | 3552 |
| gtt ccc ggc cct ccg ggc ccc cct ggg ccc cct ggg ccc cct gga acc<br>Val Pro Gly Pro Pro Gly Pro Pro Gly Pro Pro Gly Pro Pro Gly Thr<br>1185            1190            1195           1200 | 3600 |
| atg ggc gcc tcc tca ggg gtg agg ctc tgg gct aca cgc cag gcc atg<br>Met Gly Ala Ser Ser Gly Val Arg Leu Trp Ala Thr Arg Gln Ala Met<br>1205            1210            1215 | 3648 |
| ctg ggc cag gtg cac gag gtt ccc gag ggc tgg ctc atc ttc gtg gcc<br>Leu Gly Gln Val His Glu Val Pro Glu Gly Trp Leu Ile Phe Val Ala<br>1220            1225            1230 | 3696 |
| gag cag gag gag ctc tac gtc cgc gtg cag aac ggg ttc cgg aag gtc<br>Glu Gln Glu Glu Leu Tyr Val Arg Val Gln Asn Gly Phe Arg Lys Val | 3744 |

-continued

```
         1235                1240                1245
cag ctg gag gcc cgg aca cca ctc cca cga ggg acg gac aat gaa gtg    3792
Gln Leu Glu Ala Arg Thr Pro Leu Pro Arg Gly Thr Asp Asn Glu Val
    1250                1255                1260 gcc gcc ttg cag ccc ccc gtg gtg cag ctg cac gac agc aac ccc tac    3840
Ala Ala Leu Gln Pro Pro Val Val Gln Leu His Asp Ser Asn Pro Tyr
1265                1270                1275                1280 ccg cgg cgg gag cac ccc cac ccc acc gcg cgg ccc tgg cgg gca gat    3888
Pro Arg Arg Glu His Pro His Pro Thr Ala Arg Pro Trp Arg Ala Asp
                1285                1290                1295 gac atc ctg gcc agc ccc cct cgc ctg ccc gag ccc cag ccc tac ccc    3936
Asp Ile Leu Ala Ser Pro Pro Arg Leu Pro Glu Pro Gln Pro Tyr Pro
        1300                1305                1310 gga gcc ccg cac cac agc tcc tac gtg cac ctg cgg ccg gcg cga ccc    3984
Gly Ala Pro His His Ser Ser Tyr Val His Leu Arg Pro Ala Arg Pro
    1315                1320                1325 aca agc cca ccc gcc cac agc cac cgc gac ttc cag ccg gtg ctc cac    4032
Thr Ser Pro Pro Ala His Ser His Arg Asp Phe Gln Pro Val Leu His
    1330                1335                1340 ctg gtt gcg ctc aac agc ccc ctg tca ggc ggc atg cgg ggc atc cgc    4080
Leu Val Ala Leu Asn Ser Pro Leu Ser Gly Gly Met Arg Gly Ile Arg
1345                1350                1355                1360 ggg gcc gac ttc cag tgc ttc cag cag gcg cgg gcc gtg ggg ctg gcg    4128
Gly Ala Asp Phe Gln Cys Phe Gln Gln Ala Arg Ala Val Gly Leu Ala
                1365                1370                1375 ggc acc ttc cgc gcc ttc ctg tcc tcg cgc ctg cag gac ctg tac agc    4176
Gly Thr Phe Arg Ala Phe Leu Ser Ser Arg Leu Gln Asp Leu Tyr Ser
        1380                1385                1390 atc gtg cgc cgt gcc gac cgc gca gcc gtg ccc atc gtc aac ctc aag    4224
Ile Val Arg Arg Ala Asp Arg Ala Ala Val Pro Ile Val Asn Leu Lys
    1395                1400                1405 gac gag ctg ctg ttt ccc agc tgg gag gct ctg ttc tca ggc tct gag    4272
Asp Glu Leu Leu Phe Pro Ser Trp Glu Ala Leu Phe Ser Gly Ser Glu
    1410                1415                1420 ggt ccg ctg aag ccc ggg gca cgc atc ttc tcc ttt gac ggc aag gac    4320
Gly Pro Leu Lys Pro Gly Ala Arg Ile Phe Ser Phe Asp Gly Lys Asp
1425                1430                1435                1440 gtc ctg agg cac ccc acc tgg ccc cag aag agc gtg tgg cat ggc tcg    4368
Val Leu Arg His Pro Thr Trp Pro Gln Lys Ser Val Trp His Gly Ser
                1445                1450                1455 gac ccc aac ggg cgc agg ctg acc gag agc tac tgt gag acg tgg cgg    4416
Asp Pro Asn Gly Arg Arg Leu Thr Glu Ser Tyr Cys Glu Thr Trp Arg
        1460                1465                1470 acg gag gct ccc tcg gcc acg ggc cag gcc tcc tcg ctg ctg ggg ggc    4464
Thr Glu Ala Pro Ser Ala Thr Gly Gln Ala Ser Ser Leu Leu Gly Gly
    1475                1480                1485 agg ctc ctg ggg cag agt gcc gcg agc tgc cat cac gcc tac atc gtg    4512
Arg Leu Leu Gly Gln Ser Ala Ala Ser Cys His His Ala Tyr Ile Val
    1490                1495                1500 ctc tgc att gag aac agc ttc atg act gcc tcc aag          ta g      4551
Leu Cys Ile Glu Asn Ser Phe Met Thr Ala Ser Lys
1505                1510                1515
```

<210> SEQ ID NO 8
<211> LENGTH: 1516
<212> TYPE: PRT
<213> ORGANISM: Homo sapiens

<400> SEQUENCE: 8

Met Ala Pro Tyr Pro Cys Gly Cys His Ile Leu Leu Leu Leu Phe Cys

-continued

```
  1               5              10              15
Cys Leu Ala Ala Ala Arg Ala Asn Leu Leu Asn Leu Asn Trp Leu Trp
            20                  25                  30

Phe Asn Asn Glu Asp Thr Ser His Ala Ala Thr Thr Ile Pro Glu Pro
            35                  40                  45

Gln Gly Pro Leu Pro Val Gln Pro Thr Ala Asp Thr Thr His Val
            50                  55                  60

Thr Pro Arg Asn Gly Ser Thr Glu Pro Ala Thr Ala Pro Gly Ser Pro
 65                 70                  75                  80

Glu Pro Pro Ser Glu Leu Leu Glu Asp Gly Gln Asp Thr Pro Thr Ser
                85                  90                  95

Ala Glu Ser Pro Asp Ala Pro Glu Glu Asn Ile Ala Gly Val Gly Ala
               100                 105                 110

Glu Ile Leu Asn Val Ala Lys Gly Ile Arg Ser Phe Val Gln Leu Trp
           115                 120                 125

Asn Asp Thr Val Pro Thr Glu Ser Leu Ala Arg Ala Glu Thr Leu Val
       130                 135                 140

Leu Glu Thr Pro Val Gly Pro Leu Ala Leu Ala Gly Pro Ser Ser Thr
145                 150                 155                 160

Pro Gln Glu Asn Gly Thr Thr Leu Trp Pro Ser Arg Gly Ile Pro Ser
               165                 170                 175

Ser Pro Gly Ala His Thr Thr Glu Ala Gly Thr Leu Pro Ala Pro Thr
               180                 185                 190

Pro Ser Pro Pro Ser Leu Gly Arg Pro Trp Ala Pro Leu Thr Gly Pro
               195                 200                 205

Ser Val Pro Pro Ser Ser Glu Arg Ile Ser Glu Glu Val Gly Leu
       210                 215                 220

Leu Gln Leu Leu Gly Asp Pro Pro Gln Gln Val Thr Gln Thr Asp
225                 230                 235                 240

Asp Pro Asp Val Gly Leu Ala Tyr Val Phe Gly Pro Asp Ala Asn Ser
                   245                 250                 255

Gly Gln Val Ala Arg Tyr His Phe Pro Ser Leu Phe Arg Asp Phe
               260                 265                 270

Ser Leu Leu Phe His Ile Arg Pro Ala Thr Glu Gly Pro Gly Val Leu
       275                 280                 285

Phe Ala Ile Thr Asp Ser Ala Gln Ala Met Val Leu Leu Gly Val Lys
       290                 295                 300

Leu Ser Gly Val Gln Asp Gly His Gln Asp Ile Ser Leu Leu Tyr Thr
305                 310                 315                 320

Glu Pro Gly Ala Gly Gln Thr His Thr Ala Ala Ser Phe Arg Leu Pro
               325                 330                 335

Ala Phe Val Gly Gln Trp Thr His Leu Ala Leu Ser Val Ala Gly Gly
               340                 345                 350

Phe Val Ala Leu Tyr Val Asp Cys Glu Glu Phe Gln Arg Met Pro Leu
           355                 360                 365

Ala Arg Ser Ser Arg Gly Leu Glu Leu Glu Pro Gly Ala Gly Leu Phe
       370                 375                 380

Val Ala Gln Ala Gly Gly Ala Asp Pro Asp Lys Phe Gln Gly Val Ile
385                 390                 395                 400

Ala Glu Leu Lys Val Arg Arg Asp Pro Gln Val Ser Pro Met His Cys
               405                 410                 415

Leu Asp Glu Glu Gly Asp Asp Ser Asp Gly Ala Phe Gly Asp Ser Gly
               420                 425                 430
```

-continued

```
Ser Gly Leu Gly Asp Ala Arg Glu Leu Leu Arg Glu Thr Gly Ala
            435                 440                 445

Ala Leu Lys Pro Arg Leu Pro Ala Pro Pro Val Thr Thr Pro Pro
        450                 455                 460

Leu Ala Gly Gly Ser Ser Thr Glu Asp Ser Arg Ser Glu Glu Val Glu
465                 470                 475                 480

Glu Gln Thr Thr Val Ala Ser Leu Gly Ala Gln Thr Leu Pro Gly Ser
                485                 490                 495

Asp Ser Val Ser Thr Trp Asp Gly Ser Val Arg Thr Pro Gly Gly Arg
            500                 505                 510

Val Lys Glu Gly Gly Leu Lys Gly Gln Lys Gly Glu Pro Gly Val Pro
        515                 520                 525

Gly Pro Pro Gly Arg Ala Gly Pro Pro Gly Ser Pro Cys Leu Pro Gly
        530                 535                 540

Pro Pro Gly Leu Pro Cys Pro Val Ser Pro Leu Gly Pro Ala Gly Pro
545                 550                 555                 560

Ala Leu Gln Thr Val Pro Gly Pro Gln Gly Pro Pro Gly Pro Pro Gly
                565                 570                 575

Arg Asp Gly Thr Pro Gly Arg Asp Gly Glu Pro Gly Asp Pro Gly Glu
            580                 585                 590

Asp Gly Lys Pro Gly Asp Thr Gly Pro Gln Gly Phe Pro Gly Thr Pro
        595                 600                 605

Gly Asp Val Gly Pro Lys Gly Asp Lys Gly Asp Pro Gly Val Gly Glu
        610                 615                 620

Arg Gly Pro Pro Gly Pro Gln Gly Pro Pro Gly Pro Pro Gly Pro Ser
625                 630                 635                 640

Phe Arg His Asp Lys Leu Thr Phe Ile Asp Met Glu Gly Ser Gly Phe
                645                 650                 655

Gly Gly Asp Leu Glu Ala Leu Arg Gly Pro Arg Gly Phe Pro Gly Pro
            660                 665                 670

Pro Gly Pro Pro Gly Val Pro Gly Leu Pro Gly Glu Pro Gly Arg Phe
        675                 680                 685

Gly Val Asn Ser Ser Asp Val Pro Gly Pro Ala Gly Leu Pro Gly Val
        690                 695                 700

Pro Gly Arg Glu Gly Pro Pro Gly Phe Pro Gly Leu Pro Gly Pro Pro
705                 710                 715                 720

Gly Pro Pro Gly Arg Glu Gly Pro Pro Gly Arg Thr Gly Gln Lys Gly
                725                 730                 735

Ser Leu Gly Glu Ala Gly Ala Pro Gly His Lys Gly Ser Lys Gly Ala
            740                 745                 750

Pro Gly Pro Ala Gly Ala Arg Gly Glu Ser Gly Leu Ala Gly Ala Pro
        755                 760                 765

Gly Pro Ala Gly Pro Pro Gly Pro Pro Gly Pro Pro Gly Pro Pro Gly
        770                 775                 780

Pro Gly Leu Pro Ala Gly Phe Asp Asp Met Glu Gly Ser Gly Gly Pro
785                 790                 795                 800

Phe Trp Ser Thr Ala Arg Ser Ala Asp Gly Pro Gln Gly Pro Pro Gly
                805                 810                 815

Leu Pro Gly Leu Lys Gly Asp Pro Gly Val Pro Gly Leu Pro Gly Ala
            820                 825                 830

Lys Gly Glu Val Gly Ala Asp Gly Ile Pro Gly Phe Pro Gly Leu Pro
        835                 840                 845
```

```
Gly Arg Glu Gly Ile Ala Gly Pro Gln Gly Pro Lys Gly Asp Arg Gly
    850                 855                 860

Ser Arg Gly Glu Lys Gly Asp Pro Lys Asp Gly Val Gly Gln Pro
865                 870                 875                 880

Gly Leu Pro Gly Pro Gly Pro Pro Gly Pro Val Val Tyr Val Ser
                    885                 890                 895

Glu Gln Asp Gly Ser Val Leu Ser Val Pro Gly Pro Glu Gly Arg Pro
            900                 905                 910

Gly Phe Ala Gly Phe Pro Gly Pro Ala Gly Pro Lys Gly Asn Leu Gly
            915                 920                 925

Ser Lys Gly Glu Arg Gly Ser Pro Gly Pro Lys Gly Glu Lys Gly Glu
    930                 935                 940

Pro Gly Ser Ile Phe Ser Pro Asp Gly Gly Ala Leu Gly Pro Ala Gln
945                 950                 955                 960

Lys Gly Ala Lys Gly Glu Pro Gly Phe Arg Gly Pro Pro Gly Pro Tyr
                    965                 970                 975

Gly Arg Pro Gly Tyr Lys Gly Glu Ile Gly Phe Pro Gly Arg Pro Gly
            980                 985                 990

Arg Pro Gly Met Asn Gly Leu Lys Gly Glu Lys Gly Glu Pro Gly Asp
    995                 1000                1005

Ala Ser Leu Gly Phe Gly Met Arg Gly Met Pro Gly Pro Gly Pro
    1010                1015                1020

Pro Gly Pro Pro Gly Pro Pro Gly Thr Pro Val Tyr Asp Ser Asn Val
1025                1030                1035                1040

Phe Ala Glu Ser Ser Arg Pro Gly Pro Pro Gly Leu Pro Gly Asn Gln
                    1045                1050                1055

Gly Pro Pro Gly Pro Lys Gly Ala Lys Gly Glu Val Gly Pro Pro Gly
            1060                1065                1070

Pro Pro Gly Gln Phe Pro Phe Asp Phe Leu Gln Leu Glu Ala Glu Met
    1075                1080                1085

Lys Gly Glu Lys Gly Asp Arg Gly Asp Ala Gly Gln Lys Gly Glu Arg
    1090                1095                1100

Gly Glu Pro Gly Gly Gly Gly Phe Phe Gly Ser Ser Leu Pro Gly Pro
1105                1110                1115                1120

Pro Gly Pro Pro Gly Pro Arg Gly Tyr Pro Gly Ile Pro Gly Pro Lys
                    1125                1130                1135

Gly Glu Ser Ile Arg Gly Gln Pro Gly Pro Pro Gly Pro Gln Gly Pro
            1140                1145                1150

Pro Gly Ile Gly Tyr Glu Gly Arg Gln Gly Pro Pro Gly Pro Pro Gly
            1155                1160                1165

Pro Pro Gly Pro Pro Ser Phe Pro Gly Pro His Arg Gln Thr Ile Ser
    1170                1175                1180

Val Pro Gly Pro Pro Gly Pro Pro Gly Pro Pro Gly Pro Pro Gly Thr
1185                1190                1195                1200

Met Gly Ala Ser Ser Gly Val Arg Leu Trp Ala Thr Arg Gln Ala Met
                    1205                1210                1215

Leu Gly Gln Val His Glu Val Pro Glu Gly Trp Leu Ile Phe Val Ala
            1220                1225                1230

Glu Gln Glu Glu Leu Tyr Val Arg Val Gln Asn Gly Phe Arg Lys Val
            1235                1240                1245

Gln Leu Glu Ala Arg Thr Pro Leu Pro Arg Gly Thr Asp Asn Glu Val
    1250                1255                1260

Ala Ala Leu Gln Pro Pro Val Val Gln Leu His Asp Ser Asn Pro Tyr
```

-continued

```
1265                1270                1275                1280
Pro Arg Arg Glu His Pro His Pro Thr Ala Arg Pro Trp Arg Ala Asp
                1285                1290                1295
Asp Ile Leu Ala Ser Pro Pro Arg Leu Pro Glu Pro Gln Pro Tyr Pro
                1300                1305                1310
Gly Ala Pro His His Ser Ser Tyr Val His Leu Arg Pro Ala Arg Pro
                1315                1320                1325
Thr Ser Pro Pro Ala His Ser His Arg Asp Phe Gln Pro Val Leu His
                1330                1335                1340
Leu Val Ala Leu Asn Ser Pro Leu Ser Gly Gly Met Arg Gly Ile Arg
1345                1350                1355                1360
Gly Ala Asp Phe Gln Cys Phe Gln Gln Ala Arg Ala Val Gly Leu Ala
                1365                1370                1375
Gly Thr Phe Arg Ala Phe Leu Ser Ser Arg Leu Gln Asp Leu Tyr Ser
                1380                1385                1390
Ile Val Arg Arg Ala Asp Arg Ala Ala Val Pro Ile Val Asn Leu Lys
                1395                1400                1405
Asp Glu Leu Leu Phe Pro Ser Trp Glu Ala Leu Phe Ser Gly Ser Glu
                1410                1415                1420
Gly Pro Leu Lys Pro Gly Ala Arg Ile Phe Ser Phe Asp Gly Lys Asp
1425                1430                1435                1440
Val Leu Arg His Pro Thr Trp Pro Gln Lys Ser Val Trp His Gly Ser
                1445                1450                1455
Asp Pro Asn Gly Arg Arg Leu Thr Glu Ser Tyr Cys Glu Thr Trp Arg
                1460                1465                1470
Thr Glu Ala Pro Ser Ala Thr Gly Gln Ala Ser Ser Leu Leu Gly Gly
                1475                1480                1485
Arg Leu Leu Gly Gln Ser Ala Ala Ser Cys His His Ala Tyr Ile Val
                1490                1495                1500
Leu Cys Ile Glu Asn Ser Phe Met Thr Ala Ser Lys
1505                1510                1515
```

<210> SEQ ID NO 9
<211> LENGTH: 42
<212> TYPE: DNA
<213> ORGANISM: Artificial Sequence
<220> FEATURE:
<223> OTHER INFORMATION: hEST 5'primer for PCR of human endostatin gene

<400> SEQUENCE: 9
aagcttcgat cgcacagcca ccgcgacttc agccggtgc tc    42

<210> SEQ ID NO 10
<211> LENGTH: 42
<212> TYPE: DNA
<213> ORGANISM: Artificial Sequence
<220> FEATURE:
<223> OTHER INFORMATION: hEST 3'primer for PCR of human endostatin gene

<400> SEQUENCE: 10
ggatcctcat tacttggagg cagtcatgaa gctgttctca at    42

<210> SEQ ID NO 11
<211> LENGTH: 36
<212> TYPE: DNA
<213> ORGANISM: Artificial Sequence
<220> FEATURE:
<223> OTHER INFORMATION: 5'primer for PCR of mouse IgG kapa chain signal
    peptide gene

```
<400> SEQUENCE: 11
aagcttagat ctgacccaag ctggcaagcc accatg                                     36

<210> SEQ ID NO 12
<211> LENGTH: 33
<212> TYPE: DNA
<213> ORGANISM: Artificial Sequence
<220> FEATURE:
<223> OTHER INFORMATION: 3'primer for PCR of mouse IgG kapa chain signal
      peptide gene

<400> SEQUENCE: 12
ggatccgcta gcggccgcgt caccagtgga acc                                        33

<210> SEQ ID NO 13
<211> LENGTH: 114
<212> TYPE: DNA
<213> ORGANISM: mouse

<400> SEQUENCE: 13
aagcttagat ctgacccaag ctggcaagcc accatggaga cagacacact cctgctatgg           60
gtactgctgc tctgggttcc aggttccact ggtgacgcgg ccgctagcgg atcc                114

<210> SEQ ID NO 14
<211> LENGTH: 690
<212> TYPE: DNA
<213> ORGANISM: mouse

<400> SEQUENCE: 14
atgagcgtcg ctgcggtgtt tcgaggcctc cggcccagtc ctgagctgct gcttctgggc           60
ctgttgtttc tgccagcggt ggttgctgtc accagcggtg agattgggtg aagggatgct          120
agggacagga agacagttca ggagcctcag gtgcggggag gtgaactctg atgacatcgg          180
gtcatattgt atgggctttc cacctgcctt ccgagtggaa gccgatgctg taaccaagcc          240
tgtggaaagg tccagaggta ccacaccggc agatgatagg gtcatcgcta tctcttctac          300 tccctcttc ttctccccgt ttaccctcag ctggtcccga agaaagcgat ggagatctta           360
gctgtgtgtg tgtgaagacc atctcctctg ggatccatct taagcacatc accagcctgg          420
aggtgatcaa ggcaggacgc cactgtgcgg ttccccagct catgtgagtc ctgcccacat          480 ccccaggcc cgtcctctcc tctgctaccg gttccttccc atctcttccc ttcttccaac           540
caaggatctg taatgcaatt ccttcccttt ccctctttc ccctctgaca gagccaccct           600
gaagaatggg aggaaaattt gcctggaccg gcaagcaccc ctatataaga agtaatcaa           660 gaaaatcctg gagagttagg tatcagctgc                                           690

<210> SEQ ID NO 15
<211> LENGTH: 34
<212> TYPE: DNA
<213> ORGANISM: Artificial Sequence
<220> FEATURE:
<223> OTHER INFORMATION: 5'primer for PCR of mouse platelet factor-4
      gene

<400> SEQUENCE: 15
gatatcaagc ttgcaggtct tgacatgagc gtcg                                       34

<210> SEQ ID NO 16
<211> LENGTH: 34
<212> TYPE: DNA
```

```
<213> ORGANISM: Artificial Sequence
<220> FEATURE:
<223> OTHER INFORMATION: 3' primer of PCR for mouse platelet factor-4
      gene

<400> SEQUENCE: 16
gatatcctcg agggcagctg atacctaact ctcc                              34
```

COMPOSITIONS FOR GENE THERAPY OF RHEUMATOID ARTHRITIS INCLUDING A GENE ENCODING AN ANTI-ANGIOGENIC PROTEIN OR PARTS THEREOF

TECHNICAL FIELD

The present invention relates in general to compositions for gene therapy of rheumatoid arthritis including a gene encoding an anti-angiogenic protein or parts thereof, and more particularly to a gene therapy for treating rheumatoid arthritis by constructing a recombinant vector including a gene encoding an anti-angiogenic protein or parts thereof and transplanting the recombinant vector or the cells transfected or transduced with the recombinant vector into the affected area of a patient, and compositions for the gene therapy.

BACKGROUND ART

Rheumatoid arthritis is a chronic inflammatory disease involving multiple joints. The main pathology of the affected synovial tissue consists of the hyperplasia and the subintimal infiltration of T and B lymphocytes. Such inflammation of the synovial tissue is thought to be caused by T lymphocyte reactive to an unknown autoantigen. Nonetheless, the T lymphocyte infiltrated in the almost tissues does not show any indication of activation on the surface of cell and also does not almost express cytokines. In contrast to this, it is observed that both synovial tissue and fluid are enriched with the cytokines derived from macrophage. These cytokines may include interleukin-1 (IL-1) which can accelerate the growth of synovial fibroblast and tumor necrosis factors (TNFs). These experimental results suggest the hypothesis that T lymphocyte is importantly associated with the induction of inflammation to synovial tissues and the inflammation is maintained by the cytokines derived from the activated synovial cells.

One of the major intents of rheumatoid arthritis treatment is to prevent the synovial tissue hyperplasia, because it forms the pannus tissue that irreversibly destroys the cartilage and bone in the affected joint. Effective drugs for treating rheumatoid arthritis have not been developed until the present time and the developed drugs can exhibit limited efficacies. Once arthritis occurs, it causes economic loss as well as severe pain.

Medical treatments of rheumatoid arthritis being used presently are as follows. The drugs used often for initial treatment are non-steroidal anti-inflammatory drugs (NSAIDs). These NSAIDs limitedly improve a patient's condition, but cannot prevent the cartilage destruction of joint area or the progress of disease. Moreover, half the patients using this treatment should stop the treatment within one year because of serious side effect. Next, gold drugs such as gold sodium thiomalate and gold sodium thiosulfate, or disease modifying anti-rheumatic drugs (DMARDs) such as penicillamine and anti-malarials are used. These drugs also decrease the progress of rheumatoid arthritis, but after 5 years of the treatment using DMARDs, only 5–15% of the patients adhere to use the drugs because the serious side effect can be accompanied. If the drugs mentioned above are not effective any more, the affected joint area with rheumatoid arthritis should be replaced by artificial joint by surgical operation.

In this manner, most of the treatments of rheumatoid arthritis used until now were not designed with a particular target molecule and had a limitation of showing slight effects in most cases. In the meantime, it has been reported that therapeutic effects appeared by taking notice of inflammation-inducing cytokines such as TNF as a target molecule for treating the rheumatoid arthritis and introducing an antibody specific to TNF or a soluble TNF-receptor into the affected area of a patient to result in inactivation of the TNF (Maini, R. N. et al., *Immunol. Rev.* 144:195, 1995; Moreland, L. W. et al., *N. Engl. J. Med.* 337:141, 1997). In company with this, various gene transfer experiments in vivo are progressing in an animal model of rheumatoid arthritis with continuously expressing the molecules having an immune inhibitory function. Consequently, most of the current treatments are directed to correction of the immune aberration that supposedly drives the synovial cell proliferation.

Angiogenesis, the formation of new blood vessels, is one of the earliest histopathologic findings in rheumatoid arthritis and appears to be required for pannus development. This neovascularization is thought not only to maintain the chronic architectural changes via delivery of required blood-borne elements to the pannus, but also to play an active role in inflammation as a source of both cytokine and protease activity. The expanded vascular-bed volume resulting from angiogenesis may provide increased access for inflammatory cells to infiltrate the synovium. Although the factors specifically promoting angiogenesis in rheumatoid arthritis have not yet been identified, both synovial tissue and fluid are enriched with angiogenesis-promoting molecules. These include cytokines, such as basic fibroblast growth factor (bFGF), interleukin-8 (IL-8), vascular endothelial growth factor (VEGF), and soluble adhesion molecules, such as E-selectin. These data suggested a therapeutic potential for using an anti-angiogenic procedure for favorably changing the disease course of rheumatoid arthritis.

Until now a lot of factors that repress angiogenesis have been found. Most of them are created from the cleavage of protoprotein, and representatively angiostatin, endostatin and platelet factor-4 and the like have been known.

Angiostatin is composed of $98^{th}$ to $440^{th}$ amino acids of plasminogen. Angiostatin was initially isolated from mice bearing a Lewis lung carcinoma and was identified as a 38-kDa internal fragment of plasminogen that encompasses the first four kringles of the molecule (O'Relly, M. et al., *Cell* 79:715, 1994). It was reported that the growth of primary tumors was inhibited effectively by injecting purified angiostatin hypodermically in six cancer model experiments (O'Relly, M. et al, *Nat. Med* 2:689, 1996).

Endostatin consists of C-terminal 183 amino acids of collagen XVIII and has an anti-angiogenic activity. It was reported that the growth of primary tumors was inhibited effectively by injecting purified endostatin hypodermically in four cancer model experiments (O'Relly, M. et al., *Cell* 88:277, 1997).

Platelet factor-4 belongs to CXC cytokine family, which consists of chemotactic polypeptides below 10 kDa, and has an anti-angiogenic activity. It was reported that the platelet factor-4 inhibited the growth of cancer, such as B-16 melanoma and HCT-116 colon carcinoma (Maion, T. E. et al., *Cancer Research*, 51:2077, 1991).

Angiogenesis is known to be associated with various diseases, such as tumor formation and metastasis, retinitis, angioma, chronic inflammation, intestinal adhesions, atherosclerosis, rheumatoid arthritis and so on, but it has not yet been verified that anti-angiogenic factors were effective to all the diseases listed above actually. Only the tumor inhibitory effects of these factors associated with a particular disease have been reported (U.S. Pat. No. 5,856,315, U.S. Pat. No. 5,733,876, U.S. Pat. No. 5,792,845, U.S. Pat. No.

5,854,205, U.S. Pat. No. 6,024,688). The US patents discloses that the treatment effects for various kinds of diseases, such as ovarian carcinoma (HTB161, A2780S), colon carcinoma (MIP, CACO2), Lewis Lung Carcinoma (LLC), fibrosarcoma (T241), prostate gland carcinoma (PC-3) and breast carcinoma (MDA-MB), were identified by injecting anti-angiogenic factors with the type of recombinant protein.

Meanwhile, unlike general treating method that applies a toxicity to cells directly, the treating method, which cures diseases by inhibiting angiogenesis by means of supplying anti-angiogenic factors as described above, is based on the principle of inhibiting the cell growth, so anti-angiogenic factors over certain concentration should be supplied continuously to exhibit effects in vivo. But, the method of supplying anti-angiogenic factors with the type of recombinant proteins costs too much for administering proteins continuously, is troublesome and has a problem in that it imparts toxicity to a patient. Therefore, it has been required to develop a method of supplying anti-angiogenic factors to the affected area continuously and locally.

Accordingly, the present inventors have attempted new approaches for the probability of the treatment of rheumatoid arthritis by anti-angiogenesis in order to replace the prior treatment of rheumatoid arthritis having focused on solving the immunological problems. More particularly, the present inventors obtained the cell lines for producing representative anti-angiogenic factors such as angiostatin, endostatin and platelet factor-4 through inserting their genes into a viral vector and then transplanting them the affected area of mice induced with rheumatoid arthritis. We also performed the histological examinations for the level of hyperplasia in synovial cell and cartilage destruction and the immunological examinations for the concentrations of cytokines associated with the joint inflammation, as well as macroscopic examination for joint swelling to obtain the results for the progressive level of rheumatoid arthritis. The results showed that the incidence of rheumatoid arthritis in our treatment was remarkably reduced in comparison with the control group. This is to show that our gene therapy using an anti-angiogenic gene is effective to treatment of rheumatoid arthritis.

DISCLOSURE OF THE INVENTION

It is therefore an object of the present invention to provide compositions for gene therapy of rheumatoid arthritis including a DNA encoding an anti-angiogenic protein or parts thereof. More particularly, the present invention provides a recombinant vector including a DNA encoding an anti-angiogenic protein or parts thereof, a cell into which the recombinant vector is introduced and compositions for the gene therapy of rheumatoid arthritis including the recombinant vector or the recombinant cell as an active ingredient.

To accomplish this object, the present invention provides compositions for gene therapy including a DNA encoding an anti-angiogenic protein or parts thereof, which shows therapeutic effects on rheumatoid arthritis.

According to the compositions of the present invention, the DNA encoding an anti-angiogenic protein or parts thereof can be provided with an inserted form in retroviral vector, adenoviral vector, adeno-associated viral vector, herpes simplex viral vector or plasmid that can be expressed in an animal cell, or with the form of a recombinant cell that is collected by transfecting or transducing a cell with the recombinant vector including the DNA in order to supply anti-angiogenic factor to the affected area continuously and locally.

Furthermore, the present invention provides a gene therapy of treating rheumatoid arthritis by delivering the compositions to the affected area of a patient.

As used herein, the term "anti-angiogenic gene" means a DNA encoding an anti-angiogenic protein or parts thereof. It is not limited to a natural DNA, but may include any forms of proper modifications under maintenance of anti-angiogenic activity and additions of elements for expression regulation if it can be used suitably for the purpose of the present invention, regardless of whether or not it is obtained by genetic engineering method or chemical method.

Hereinafter, the present invention will be described in detail.

The present invention is characterized in that the composition for gene therapy of treating arthritis comprises a DNA encoding anti-angiogenic protein or parts thereof as an active ingredient. The anti-angiogenic gene used in the gene therapy for treating arthritis according to the present invention is preferably a gene encoding at least one protein selected from the group consisting of angiostatin, endostatin, platelet factor-4, thrombospondin-1, thrombospondin-2, METH-1, METH-2 (anti-angiogenic proteins having metalloprotease domain and thrombospondin domain; Vanzquez F. et al., *J. Biol. Chem.* 274(33):23349–57, 1999) and hepatocyte growth factor.

Particularly, the anti-angiogenic gene included in the composition for gene therapy of treating arthritis according to the invention is preferably the gene encoding the angiostatin including $98^{th}$ to $440^{th}$ amino acids of human plasminogen and the four kringles, the gene encoding the endostatin including $1334^{th}$ to $1516^{th}$ amino acids of human collagen XVIII, or the gene encoding the mouse platelet factor-4 protein.

Although an entire amino acid sequence may be used as the anti-angiogenic factor, a fragment known as having anti-angiogenic activity may also be used. For example, angiostatin kringle 1–3 fragment may be used for this purpose.

The example of the anti-angiogenic gene included in the composition for gene therapy of treating arthritis according to the invention may preferably be the DNA derived from human, mouse, rhesus, pig or bovine plasminogen, and more preferably the cDNA of human angiostatin. The endostatin gene may also preferably be the DNA derived from human, mouse, rhesus, pig or bovine collagen XVIII, and more preferably the cDNA of human endostatin. The preferable embodiments of the invention identified that the angiostatin and endostatin genes cloned from human foreskin fibroblast (HFF) are effective to gene therapy for treating arthritis.

The recombinant vector included in the composition for gene therapy for treating arthritis according to the invention also comprises the anti-angiogenic gene. It is preferable that the recombinant vector further comprises a nucleotide sequence encoding a signal peptide required for secretion in the upstream or downstream in order to secrete the protein expressed by the gene out of the cell.

The signal peptide may include any signal peptides known as associated to protein secretion in eukaryotic cell, and may preferably be 18 of amino-terminal amino acids of human plasminogen represented as the SEQ ID No. 2 or the signal peptide of mouse immunoglobulin κ chain encoded by the nucleotide sequence represented as SEQ ID No. 13.

For example, as described below in one preferable example according to the invention, the signal sequence can be functionally connected to the anti-angiogenic gene by synthesizing a nucleotide including the nucleotide sequence encoding 18 of the amino-terminal amino acids of human plasminogen and the sequences having restrictive enzyme cleaving sites, hybridizing it into double helical DNA, and treating it with restrictive enzyme to insert it into a certain site of target vector. However, the construction of vector having a signal sequence for producing the secretion type of anti-angiogenic protein is not limited to as mentioned above, but may be accomplished by the method well known in the field of this art.

The vector used in the composition for gene therapy of treating arthritis according to the invention is a vector in which the anti-angiogenic gene can be inserted to supply the anti-angiogenic factor continuously to the affected area. The vector may include virus-derived vectors such as retroviral vector, adenoviral vector, adeno-associated viral vector, and herpes simplex viral vector, plasmids capable of being expressed in bodies of animals such as pCXN2 (Gene, 108:193–200, 1991) and PAGE207 (Japan Patent Laid-Open No. Sho6-4684), and their modified vectors.

In the preferable example according to the present invention, a viral vector was prepared, which was to produce angiostatin, endostatin or platelet factory as a anti-angiogenic factor, using MT5 retroviral vector which had been filed before Korean Industrial Property Office (KIPO) by the present inventors (Korean Patent Appl. No. 97-48095; KCCM-10205), and the effect for treating arthritis was verified by experimental results as to mouse using the viral vector. The MT5 retroviral vector is a vector based on murine leukemia virus (MLV) including mutant noncoding sequence of human elongation factor 1 (EF 1), without coding sequence derived from virus and is good in both external gene expressing efficiency and viral titer. That is to say, the vector is to enhance stability by completely removing the gag, pol and env sequence of MLV, is to include at the upstream of external gene insertion site, a part of noncoding sequence of EF 1a as a noncoding sequence derived from heterogeneous gene for providing splicing receptor, and is to control splicing efficiency appropriately to maintain gene expressing highly with also maintaining virus producing concentration highly.

Particularly, in one example of the present invention, angiostatin DNA fragment encoding $93^{rd}$ to $368^{th}$ amino acids of human plasminogen represented as SEQ ID No. 2 was obtained from human foreskin fibroblast (HFF) through PCR and was inserted into pGEM T easy vector to construct pGEM T easy-hASTi vector. The sequence encoding 18 of amino-terminal amino acids of plasminogen of SEQ ID No. 2 was synthesized as a signal sequence, and was inserted into pGEM T easy-hASTi vector to construct pGEM T easy-hAST vector. The obtained vector was cleaved with BamHI to prepare human angiostatin gene fragment connected with the signal sequence, which was inserted into MT5 vector. In the meantime, to prepare cell lines expressing human angiostatin, MT5-hAST vector DNA was transfected into 293T cell with the plasmid expressing gag-pol and env gene of murine leukemia virus and then non-cellular virus was obtained from the cell culture media.

The obtained virus was transduced into NIH3T3, and then the cell lines introduced with retrovirus were selected and cultivated to prepare NIH3T3 cells expressing human angiostatin protein. By means of the same method, NIH3T3 cells expressing human endostatin protein and mouse platelet factor-4 protein were prepared respectively.

Another example of the present invention verified the effect of gene therapy for arthritis using the cell lines respectively expressing anti-angiogenic proteins such as human angiostatin protein, human endostatin protein and mouse platelet factor-4 protein.

Particularly, a gene therapy to mice without any macroscopic signs of inflammation in collagen-induced arthritis mouse model was performed. Namely, anti-angiogenic protein-producing NIH3T3 cell lines mixed with PBS were transplanted in the knee joint area of rear leg of the arthritis-mouse, and then the progressive level of arthritis was investigated by measuring joint swelling, synovial hyperplasia, destruction of cartilage, and joint inflammation-associated cytokine level.

The results showed that the swelling level in the knee joint area in case of transplanting angiostatin-producing NIH3T3 cell lines was remarkably decreased to 27% in comparison that the control group in case of injecting only PBS or transplanting the cell lines transferred with only MT5 vector was 47% or 67%. The frequency showing the significant level of IL-1 was also remarkably decreased. The synovial hyperplasia and cartilage destruction in the knee joint area were also remarkably decreased. Furthermore, similar results to the transplant of antiostatin producing NIH3T3 cell lines were obtained when endostatin producing NIH3T3 cell lines and platelet factor-4 producing NIH3T3 cell lines were transplanted. These results show that the gene therapy using anti-angiogenic gene according to the present invention is effective to suppression and treatment of arthritis.

In another example of the present invention, duration of therapeutic effects was measured. The result showed that therapeutic effect of a single injection lasts for 14 days after treatment.

The composition of gene therapy for treating arthritis according to the present invention can be prepared by preparing viral particles including recombinant DNA encoding anti-angiogenic protein or cell lines transduced with the viral particles and mixing them with carriers used in gene therapy (Crystal R G et al., Nature Genet. 8:42–51, 1994).

The carriers used in gene therapy may include any carriers generally used in injection liquid. For example, the carriers may include distilled water, sodium chloride solutions, the mixtures of sodium chloride and inorganic salts or their similar mixtures, the solutions of materials such as mannitol, lactose, dextran, and glucose, amino acid solutions such as glycine and arginine, the mixtures of organic acid solutions or salt solutions and glucose solutions, and their similar solutions. The injection liquid may be prepared in the form of solution, suspension or colloidal solution by adding osmotic modulator, pH controller, vegetable oil such as sesame oil or bean oil, lecithin or surfactant such as non-ionic surfactant to the carriers in the conventional manners. This injection may be prepared in the form of powder or lyophilization and then dissolved in the form of solution before being used.

The composition of gene therapy for treating arthritis according to the present invention may be dissolved in a sterilized carrier, in case of solid phase, if needed, before treatment of gene therapy, or may be used as it is without further treatment in case of liquid phase.

The composition of gene therapy for treating arthritis according to the present invention can be absorbed in the synovial cell of blood vessel of target area through the injection manner that the total daily dose of effective ingredient locally administered to a patient may range from 1 ng to 1 g or it may be administered once through catheter after surgical operation.

The cell line including anti-angiogenic factor producing vector may be any cell which has the major histocompatibility complex (MHC) antigen identical or similar to patient's such that it does not generate histoincompatibility during transplantation. That the synovial cell of patient's are separated and used for gene transfer is preferable for excluding histoincompatibility completely.

BRIEF DESCRIPTION OF THE DRAWINGS

FIG. 1 is a schematic diagram that shows the process of preparing the pGEM T-hASTi vector by cloning human angiostatin gene through PCR and introducing the cloned gene into pGEM T easy vector, the process of preparing the pGEM T-hAST vector by linking the signal sequence obtained through PCR functionally to the upstream of the angiostatin gene introduced in pGEM T-hASTi vector, and the process of preparing the MT5-hAST vector by introducing the angiostatin gene linked to the signal peptide into the BamHI site of retroviral MT5 vector.

FIG. 2 is a schematic diagram that shows the structure of a double stranded DNA produced by hybridizing two synthetic nucleotides, which were prepared to have the nucleotide sequences represented by SEQ. ID. NO:5 and SEQ. ID. NO:6, and the amino acid sequence of the signal peptide encoded therefrom represented by residues 1 to 18 of SEQ ID NO:2, in order to obtain a gene that encodes the signal peptide consisting of N-terminal 18 amino acids of human plasminogen.

FIG. 4 shows photographs illustrating the level of cartilage destruction by staining with Safranin O/fast green, knee joint area in the collagen-induced arthritis (CIA) mice, into which NIH3T3 cell line expressing angiostatin (B) and NIH3T3 control cell line transduced with only MT5 vector not including an angiostatin gene (A) are injected, respectively.

■ : control group

Figure 3:
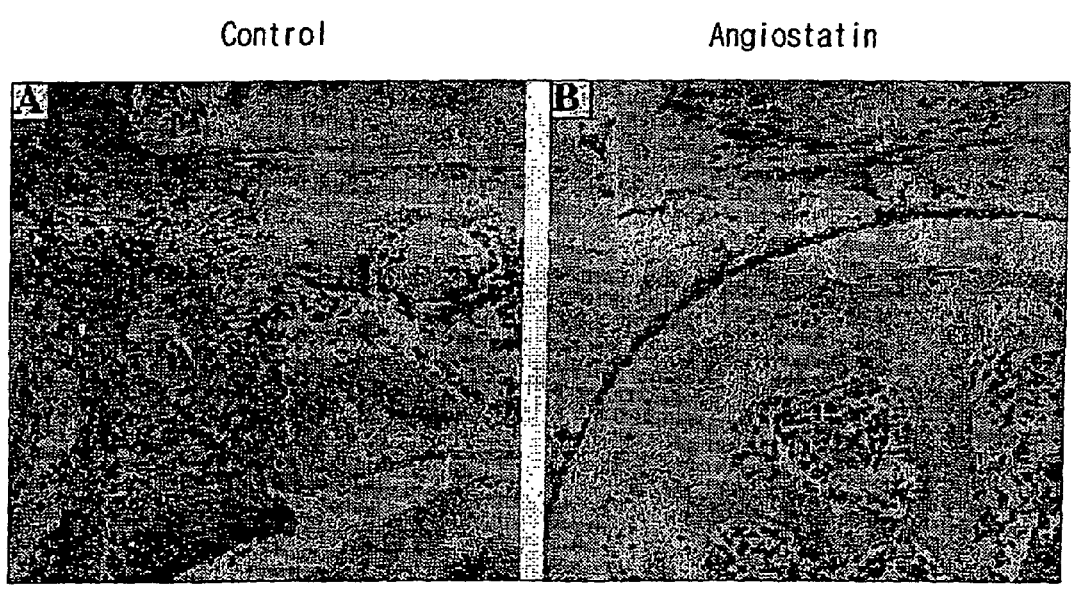
FIG. 3 shows photographs illustrating the level of hyperplasia by staining with hematoxylin/eosin, knee joint area in the collagen-induced arthritis (CIA) mice, into which NIH3T3 cell line expressing angiostatin (B) and NIH3T3 control cell line transduced with only MT5 vector not including an angiostatin gene (A) are injected, respectively.

● : group transplanted with 1×10⁵ of angiostatin-expressing NIH3T3 cells

*: P<0.05 **: P<0.06

BEST MODE FOR CARRYING OUT THE INVENTION

The present invention will hereinafter be described in further detail by examples. It should however be borne in mind that the present invention is not limited to or by examples.

EXAMPLE 1

Construction of Retroviral Vector Introduced with a Gene Encoding an Anti-Angiogenic Protein (1-1) Construction of Retroviral Vector Introduced with Human Angiostatin Gene (1-1-1) Cloning of Human Angiostatin Gene (Construction of pGEM T Easy-hASTi Vector)

Human angiostatin gene was cloned by extracting RNA from the human foreskin fibroblast (HFF), obtaining cDNA, and performing PCR. First, RNA was extracted from the HFF cells by using the Tryzol method (Gibco BRI, USA), and cDNA was obtained from the extracted RNA by using reverse transcriptase polymerization reaction. Then, a DNA fragment including human angiostatin gene was obtained through the PCR by using the cDNA as a PCR template and the synthetic nucleotides represented by SEQ. ID. NO:3 and SEQ. ID. NO:4 as primers. To perform the PCR, total 100 μl of a mixture solution was prepared by mixing 1 μl of template DNA, each of 1 μl of 10 pmol/μl primer, 10 μl of 10 mM dNTP, 35 units of Expand high fidelity enzyme (Gibco BRL, USA) and 10 μl of buffer for enzymes. The reaction condition for PCR was as follows: 94° C. for 1 min, 50° C. for 1 min, 72° C. for 1 min 30 sec. The PCR was performed 30 cycles. The amplified angiostatin gene includes a DNA encoding $93^{rd}$~$368^{th}$ amino acids of human plasminogen represented by SEQ. ID. NO:2. The amplified PCR product of about 800 bp was introduced into a pGEM T easy vector (Promega, Wis., USA) to construct a pGEM T easy-hASTi vector (See FIG. 1).

(1-1-2) Linking of Signal Sequence and Construction of Retroviral MT5-hAST Vector To make the protein secreted out of cells after expressed from the human angiostatin gene cloned in the above Example (1-1-1), a nucleotide sequence encoding a signal peptide was linked functionally to the upstream of the angiostatin gene. The signal sequence was introduced into the pGEM T easy-hASTi vector. Particularly, to prepare a nucleotide sequence encoding N-terminal 18 amino acids of human plasminogen as a signal peptide, nucleotides represented by SEQ. ID. NO:5 and SEQ. ID. NO:6 were synthesized. The synthetic nucleotides were mixed, incubated for 1 min at 94° C., and consequently incubated for 1 min 30 sec at 50° C. to form a double stranded DNA by pairing the two synthetic nucleotides each other. As shown in FIG. 2, the double stranded synthetic nucleotides have HindIII and BamHI sites in one end, and NheI site in the other end. The nucleotides were introduced into HindIII and NheI sites of the pGEM T easy-hASTi vector to construct a pGEM T easy-hAST vector. And then, the pGEM T easy-hAST vector was digested with BamHI to obtain human angiostatin gene linked to the signal sequence, and the obtained human angiostatin gene was introduced into the BamHI site of the MT5 vector (KCCM-10205) to construct a MT5-hAST vector (FIG. 1).

(1-2) Construction of Retroviral Vector Introduced with Human Endostatin Gene (1-2-1) Cloning of Human Endostatin Gene (Construction of pGEM T Easy-hESTi Vector)

Human endostatin gene was cloned by extracting RNA from the human foreskin fibroblast (HFF), obtaining cDNA, and performing PCR. A DNA fragment including human endostatin gene was obtained by the same method and under the same PCR condition as the Example (1-1-1) above, except for using the synthetic nucleotides represented by SEQ. ID. NO:9 and SEQ. ID. NO:10 as primers. The amplified endostatin gene includes a DNA encoding $1334^{th}$~$1516^{th}$ amino acids of human collagen XVIII represented by SEQ. ID. NO:8. The amplified PCR product of about 550 bp was introduced into a pGEM T easy vector (Promega, Wis., USA) to construct a pGEM T easy-hESTi vector.

(1-2-2) Linking of Signal Sequence and Construction of Retroviral MT5-hEST Vector To make the protein secreted out of cells after expressed from the human endostatin gene cloned in the above Example (1-2-1), a nucleotide sequence encoding a signal peptide was linked functionally to the upstream of the endostatin gene. The signal sequence was introduced into the pGEM T easy-hESTi vector. Particularly, to prepare a nucleotide sequence encoding N-terminal 25 amino acids of mouse immunoglobulin kappa chain as a signal peptide, PCR was performed by using the pSecTag plasmid (Invitrogen) DNA as a template, and synthetic nucleotides represented by SEQ. ID. NO: 11 and SEQ. ID. NO:12 as primers. To perform the PCR, total 100 μl of a mixture solution was prepared by mixing 1 μl of template DNA, each of 1 μl of 10 pmol/μl primer, 10 μl of 10 mM dNTP, 3.5 units of Expand high fidelity enzyme (Gibco BRL, USA) and 10 μl of buffer for enzymes. The reaction condition for PCR was as follows:94° C. for 1 min, 50° C. for 1 min, 72° C. for 1 min 30 sec. The PCR was performed 30 cycles. The signal sequence of the amplified mouse immunoglobulin kappa chain is represented by SEQ. ID. NO:13. The amplified PCR product of about 120 bp was introduced into a pGEM T easy vector (Promega, Wis., USA) to construct a pGEM T easy-SigPep vector. And then, the pGEM T easy-hESTi vector was digested with NheI/BamHI to obtain endostatin gene, and the obtained endostatin gene was introduced into the NheI/BamHI sites of the pGEM T easy-SigPep plasmid to construct a pGEM T easy-hEST vector. Consequently, the pGEM T easy-hEST plasmid was digested with BglII/BamHI to obtain human endostatin gene linked to the signal sequence, and the obtained human endostatin gene was introduced into the BamHI site of the MT5 vector (KCCM-10205) to construct a MT5-hEST vector.

(1-3) Construction of Retroviral Vector Introduced with Mouse Platelet Factor-4 Gene (1-3-1) Cloning of Mouse Platelet Factor-4 Gene (Construction of pGEM T Easy-mPF4 Vector)

Mouse platelet factor-4 gene was cloned by extracting RNA from the spleen of the C57BL/6 mouse (Japan SLC, Hamamatsu, Japan), obtaining cDNA, and performing PCR. First, RNA was extracted from the spleen tissue of the mouse by using the Tryzol method (Gibco BRL, USA), and cDNA was obtained from the extracted RNA by using reverse transcriptase polymerization reaction. Then, a DNA fragment including mouse platelet factor-4 gene was obtained through the PCR by using the cDNA as a PCR template and the synthetic nucleotides represented by SEQ. ID. NO:15 and SEQ. ID. NO:16 as primers. To perform the PCR, total 100 μl of a mixture solution was prepared by mixing 1 μl of template DNA, each of 1 μl of 10 pmol/μl primer, 10 μl of 10 mM dNTP, 3.5 units of Expand high fidelity enzyme (Gibco BRL, USA) and 10 μl of buffer for enzymes. The reaction condition for PCR was as follows:94° C. for 1 min, 50° C. for 1 min, 72° C. for 1 min 30 sec. The PCR was performed 30 cycles. The amplified platelet factor-4 gene is represented by SEQ. ID. NO:14. The amplified PCR product of about 380 bp was introduced into a pGEM T easy vector (Promega, Wis., USA) to construct a pGEM T easy-mPF4 vector.

(1-3-2) Construction of Retroviral MT5-mPF4 Vector

The pGEM T easy-mPF4 vector prepared in the Example (1-3-1) above was digested with EcoRV to obtain the platelet factor-4 gene. The obtained platelet factor-4 gene was digested with BamHI, treated with Klenow fragment, and then was introduced into the blunt-ended MT5 vector (KCCM-10205) to construct a MT5-mPF4 vector.

EXAMPLE 2

Preparation of Cell Lines Expressing Anti-Angiogenic Protein (2-1) Preparation of Cell Lines Expressing Human Angiostatin In order to prepare cell lines expressing human angiostatine, the retrovirus including the MT5-hAST vector was produced. At first, the MT5-hAST vector DNA prepared in the example (1-1-2) described above was transfected into 293 T cells with the plasmid (retrovirus packaging kit ampho catalogue #6161; TAKARA SHUZO CO., LTD., SHIGA, Japan) expressing gag-pol and env gene of murine leukemia virus (MLV) and after 8 hrs, new culture medium was exchanged. After 48 hrs, the cell culture medium was filtered with 0.45 μm of filter paper to obtain noncellular virus.

The produced MT5-hAST retrovirus was transduced into NIH3T3 cells (ATCC CRL1658), and then the cells were treated with G418 (1 μg/μl, Gibco BRL, USA) for 14 days after 24 hrs to select and cultivate the cell lines introduced with the retrovirus. Collecting the group of cells selected and cultivated gave rise to preparation of NIH3T3 cell lines expressing human angiostatin protein.

(2-2) Preparation of Cell Lines Expressing Human Endostatin

NIH3T3 cell lines expressing human endostatin protein was prepared according to the same method as the example (2-1), except using the MT5-hEST vector prepared in the example (1-2-2) instead of the MT5-hAST vector.

(2-3) Preparation of Cell Lines Expressing Mouse Platelet Factor-4

NIH3T3 cell lines expressing platelet factor-4 protein was prepared according to the same method as the example (2-1), except using the MT5-mPF vector prepared in the example (1-3-2) instead of the MT5-hAST vector.

EXAMPLE 3

Efficacy of Gene Therapy Using Anti-Angiogenic Factors in Mouse Collagen-Induced Arthritis Model (3-1) Preparation of Mouse Collagen-Induced Arthritis Model Mouse collagen-induced arthritis (CIA) model is an autoimmune type of arthritis model which shows many characteristics in common with human rheumatoid arthritis. The collagen-induced arthritis model was prepared by the following method. DBA/1 mice (Jackson Laboratory, Maine, USA), aged 9–10 weeks at the start of experiments, were immunized intradermally at the base of the tail with bovine type II collagen (100 μg; Chondrex, Wash., USA) emulsified in Freund's complete adjuvant (Gibco BRL, NY, USA). On day 21, the animals were boosted with an intradermal injection of 100 μg type II collagen. Gradual onset of arthritis normally starts approximately 4 weeks after initial immunization. In this example, mice that did not yet have any macroscopic signs of arthritis were chosen at 30 days after the initial immunization to perform gene therapy.

(3-2) Measurement of Arthritis Progress Level

Measurement and detailed decision on indices for measuring arthritis progress level were performed by the following manner. First, histological analysis was performed for the knee joint cavity in which the cell lines expressing anti-angiogenic protein (human angiostatin, human endostatin, and mouse platelet factor-4) were transplanted. The main phathology of rheumatoid arthritis may be summarized to consist of the hyperplasia of joint synovial cells and irreversible destruction of cartilage tissues due to the hyperplasia. Histological analysis is the most effective to decide the progress level of the synovial cell hyperplasia and cartilage destruction. For this analysis, knee joints of mice were dissected, fixed in 10% phosphate-buffered formalin, decalcified in 10% EDTA, and then embedded in paraffin. Standard frontal sections of 7 μm were prepared and stained with either hematoxylin/eosin or Safranin O/fast green (Bakker A. C. et al., *Arthritis and Rheumatism* 40:893–900, 1997; Apparailly Florence et al., *J. Immunol.* 160:5213–5220, 1998).

The hyperplasia levels of synovial cells were scored based on the results of hematoxylin/eosin stain according to the criterion suggested in the published paper (Apparailly Florence et al., *J. Immunol.* 160:5213–5220, 1998; Lubberts Erik et al., *J. Immunol.* 163:4546–4556, 1999). The scores are 0 in normal condition, 1 in slight inflammation and faint synovial hyperplasia, and 2 in the formation of pannus and synovial hyperplasia heavier than severe level. It was decided that arthritis occurred in the knee if the hyperplasia level of synovial cell was 2 or more.

The levels of cartilage destructions were scored based on the results of Safranin O/fast green stain according to the criterion suggested in the published paper (Lubberts Erik et al., *J. Immunol.* 163:4546–4556, 1999). The scores are 0 in normal condition, 1 in vacuolation of cartilage cell and slight loss of proteoglycan, 2 in the observation of cartilage erosion in addition to the previous, and 3 in cartilage erosions at two or more regions and destruction of subchondral layer. It was decided that arthritis occurred in the knee if the level of cartilage destruction was 2 or more.

Neovascularization level in the joint area was investigated by performing immunohistochemical stain using the antibody specific to CD31, a surface protein of vascular endothelial cell (Xu, M. et al., *Molecular Genetics and Metabolism* 63:103–109, 1998).

The progress level of arthritis in the ankle area was determined with macroscopic sign such as joint swelling and immunological sign such as the expression amount of inflammation-associated cytokine. The levels of joint swellings were scored based on the results of macroscopic signs according to the criterion suggested in the published paper (Apparailly Florence et al., *J. Immunol.* 160:5213–5220, 1998). The scores are 0 in normal condition, 1 in swelling and slight erythema, 2 in distint swelling and erythema, and 3 in severe edema accompanied with wound. It was decided that arthritis occurred in the ankle if the level of joint swelling was 2 or more. It was also decided to be a serious case of arthritis if the level was 3 or more. The detection of inflammation-associated cytokine was performed by measuring the expression amount of mouse interleukine-1 (IL-1), which was known to play an important role during the progress of arthritis, in the ankle joint with ELISA (R&D systems, Minneapolis, USA) according to the instruction of manufacturer. It was decided that arthritis occurred if the expression amount of interleukine-1 was 10 ng or more per 1 g of proteins in the joint tissue.

Figure 5:
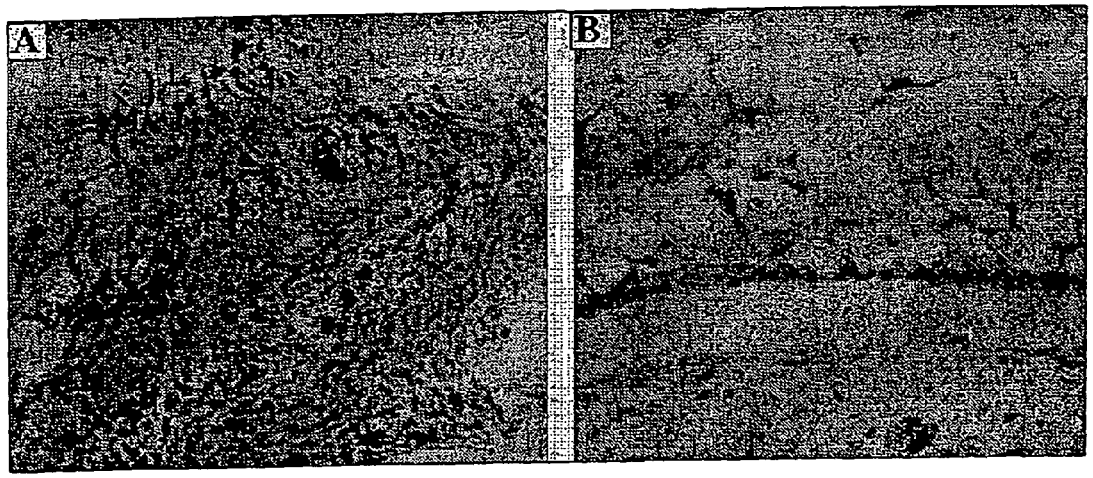
FIG. 5 shows photographs illustrating the neovascularization level investigated using an antibody specific to CD31, which is surface protein of vascular endothelial cell by immunohistochemically staining knee joint area in the collagen-induced arthritis (CIA) mice, into which NIH3T3 cell line expressing angiostatin (B) and NIH3T3 control cell line transduced with only MT5 vector not including an angiostatin gene (A) are injected, respectively.

(3-3) Implementation of Gene Therapy and Analysis of Experimental Results (3-3-1) In Case of Transplanting NIH3T3 Cell Lines Expressing Human Angiostatin Protein In one group were selected 15 of mice. The NIH3T3 cell lines expressing human angiostatin were transplanted by mixing $1 \times 10^5$ of the NIH3T3 cell lines with 25 μl of PBS solution in aseptic condition and injecting the mixture into the knee joint cavity of mouse using a syringe of 30 gauge. Into one negative control group, NIH3T3 cells transferred with only MT5 vector were transplanted, and into another negative control group, only PBS was injected. After that time, the arthritis progresses were observed. On day 10 after the transplantation of the cell lines, the progressive levels of arthritis were measured by the investigation of macroscopic sign such as joint swelling, histological signs such as joint synovial cell hyperplasia and cartilage destruction, and immunological sign such as the level of joint inflammation-associated cytokine. The neovascularization in the joint area was also investigated using immunohistochemical stain. The results are shown in Table 1 and FIGS. 3 through 5.

TABLE 1

The incidences of arthritis for each item

| | Ankle joint swelling (%) | Synovial cell hyperplasia (%) | Joint cartilage destruction (%) | IL-1 detection (%) |
|---|---|---|---|---|
| PBS | 47 | 65 | 53 | 41 |
| MT5 | 67 | 93 | 67 | 67 |
| MT5-hAST | 27 | 47 | 33 | 27 |

As shown in Table 1, in the results of joint swelling in the ankle of mouse rear leg, the level of joint swelling in case of transplanting the cells expressing angiostatin was remarkably decreased as compared to those in cases of control groups. Namely, when the incidence of arthritis was investigated based on the joint swelling, the incidence of arthritis was seen in 27% in case of transplanting the cells expressing angiostatin, while the incidences of arthritis was respectively seen in 67% and 47% in cases of transplanting the control cell lines and of injecting only PBS. These results verified that the incidence of arthritis in the cells expressing angiostatin was significantly decreased.

In the results obtained through the investigation of synovial cell hyperplasia in the knee joint of mouse rear leg as shown in FIG. 3, the growth of synovial cell in case of transplanting the cells expressing angiostatin was remarkably decreased as compared to those in cases of the control groups. Namely, when the incidence of arthritis was investigated based on the synovial cell hyperplasia, the incidence of arthritis was seen in 47% in case of transplanting the cells expressing angiostatin, while the incidences of arthritis was respectively seen in 93% and 65% in cases of transplanting the control cell lines and of injecting only PBS. These results verified that the incidence of arthritis in the cells expressing angiostatin was significantly decreased.

In the results obtained through the investigation of the desctruction of cartilage tissue in the knee joint of mouse rear leg as shown in FIG. 4, the destruction of cartilage tissue in case of transplanting the cells expressing angiostatin was remarkably decreased as compared to those in cases of the control groups. Namely, when the incidence of arthritis was investigated based on the destruction of cartilage tissue, the incidence of arthritis was seen in 33% in case of transplanting the cells expressing angiostatin, while the incidences of arthritis was respectively seen in 67% and 53% in cases of transplanting the control cell lines and of injecting only PBS. These results verified that the incidence of arthritis in the cells expressing angiostatin was significantly decreased.

In the results of the neovascularization level in the knee joint of mouse rear leg obtained by performing immunohistochemical stain using antibody specific to CD31, a surface protein in vascular endothelial cell as shown in FIG. 3, the level of neovascularization in case of transplanting the cells expressing angiostatin was remarkably decreased as compared to that in case transplanted with the control cell lines.

The concentration of IL-1 in the ankle joint of mouse rear leg in case of transplanting the cells expressing angiostatin into the knee of the same leg was remarkably decreased as compared to those in cases of the control groups. Namely, in the results obtained through the investigation of the frequency in case that the concentration of IL-1 is 10 ng or more per 1 g of the joint tissue, the frequency was 27% in case of transplanting the cells expressing angiostatin, while the frequency was 67% in case of transplanting the control cell lines and 41% in case of injecting only PBS. These results verified that the frequency showing the significant level of IL-1 was remarkably decreased in the cells expressing angiostatin.

The total results described as above showed that the transplantation of the cells expressing angiostatin into the knee with occurrence of arthritis remarkably decreased the incidence of arthritis not only in the knee joint but also in the ankle joint of the same leg. These results may suggest that when a gene therapy is performed in a large joint such as knee joint, the treatment effect can be also showed in a small joint such as ankle joint of the same leg by movements of inflammation-inducible or inflammation-inhibitory factors along with the flow of fluid connected between the joints.

(3-3-2) In Case of Transplanting NIH3T3 Cell Lines Expressing Human Endostatin Protein In one group were selected 15 of mice. The NIH3T3 cell lines expressing human endostatin were transplanted by mixing $1 \times 10^5$ of the NIH3T3 cell lines with 25 µl of PBS solution in aseptic condition and injecting the mixture into the knee joint cavity of mouse using a syringe of 30 gauge. Into one negative control group, NIH3T3 cells transferred with only MT5 vector were transplanted. After that time, the arthritis progresses were observed, and macroscopic sign such as joint swelling was investigated. The results are shown in Table 2.

TABLE 2

The incidences of arthritis

| | Ankle joint swelling (%) |
|---|---|
| MT5 | 75 |
| MT5-hEST | 23 |

As shown in Table 2, in the results of joint swelling in the ankle of mouse rear leg, the level of joint swelling in case of transplanting the cells expressing endostatin was remarkably decreased as compared to that in case of the control group. Namely, when the incidence of arthritis was investigated based on the joint swelling, the incidence of arthritis was seen in 23% in case of transplanting the cells expressing endostatin, while the incidence of arthritis was seen in 75% in case of transplanting the control cell lines. These results verified that the incidence of arthritis in the cells expressing endostatin was significantly decreased. These results may also suggest that the gene therapy using endostatin can effectively inhibit the occurrence of arthritis.

(3-3-3) In Case of Transplanting NIH3T3 Cell Lines Expressing Mouse Platelet Factor-4 Protein In one group were selected 15 of mice. The NIH3T3 cell lines expressing platelet factor-4 were transplanted by mixing $1 \times 10^5$ of the NIH3T3 cell lines with 25 µl of PBS solution in aseptic condition and injecting the mixture into the knee joint cavity of mouse using a syringe of 30 gauge. Into one negative control group, NIH3T3 cells transferred with only MT5 vector were transplanted. After that time, the arthritis progressions were observed. The progressive levels of arthritis were measured by the investigation of macroscopic sign such as joint swelling, histological signs such as joint synovial cell hyperplasia and cartilage destruction, and immunological sign such as the level of joint inflammation-associated cytokine. The results are shown in Table 3.

TABLE 3

The incidences of arthritis for each item

| | Ankle joint swelling (%) | Synovial cell hyperplasia (%) | Joint cartilage destruction (%) | IL-1 detection (%) |
|---|---|---|---|---|
| MT5 | 64 | 77 | 54 | 64 |
| MT5-hAST | 29 | 43 | 36 | 29 |

As shown in Table 3, in the results of joint swelling in the ankle of mouse rear leg, the level of joint swelling in case of transplanting the cells expressing platelet factor-4 was remarkably decreased as compared to that in case of the control group. Namely, when the incidence of arthritis was investigated based on the joint swelling, the incidence of arthritis was seen in 29% in case of transplanting the cells expressing platelet factor-4, while the incidence of arthritis was seen in 64% in case of transplanting the control cell lines. These results verified that the incidence of arthritis in the cells expressing platelet factor-4 was significantly decreased.

In the results obtained through the investigation of synovial cell hyperplasia in the knee joint of mouse rear leg, the growth of synovial cell in case of transplanting the cells expressing platelet factor-4 was remarkably decreased as compared to that in case of the control group. Namely, when the incidence of arthritis was investigated based on the synovial cell hyperplasia, the incidence of arthritis was seen in 43% in case of transplanting the cells expressing platelet factor-4, while the incidence of arthritis was seen in 77% in case of transplanting the control cell lines. These results verified that the incidence of arthritis in the cells expressing platelet factor-4 was significantly decreased.

In the results obtained through the investigation of the destruction of cartilage tissue in the knee joint of mouse rear leg, the destruction of cartilage tissue in case of transplanting the cells expressing platelet factor-4 was remarkably decreased as compared to that in case of the control group. Namely, when the incidence of arthritis was investigated based on the destruction of cartilage tissue, the incidence of arthritis was seen in 36% in case of transplanting the cells expressing platelet factor-4, while the incidence of arthritis was seen in 54% in case of transplanting the control cell lines. These results verified that the incidence of arthritis in the cells expressing platelet factor-4 was significantly decreased.

The concentration of IL-1 in the ankle joint of mouse rear leg in case of transplanting the cells expressing platelet factor-4 into the knee of the same leg was remarkably decreased as compared to that in case of the control group. Namely, in the results obtained through the investigation of the frequency in the case that the concentration of IL-1 is 10 ng or more per 1 g of the joint tissue, the frequency was 29% in case of transplanting the cells expressing platelet factor-4, while the frequency was 64% in case of transplanting the control cell lines. These results verified that the frequency showing the significant level of IL-1 was remarkably decreased in the cells expressing platelet factor-4.

The total results described as above showed that the transplantation of the cells expressing platelet factor-4 into the knee with occurrence of arthritis remarkably decreased the incidence of arthritis not only in the knee joint but also in the ankle joint of the same leg.

EXAMPLE 4

Measurement for Duration of Therapeutic Effects

To measure the duration of therapeutic effect for NIH3T3 cell lines expressing angiostatin, the NIH3T3 cell lines were transplanted by mixing $1 \times 10^5$ of the NIH3T3 cell lines with 25 μl of PBS solution in aseptic condition and injecting the mixture into the knee joint cavity of mouse using a syringe of 30 gauge. Into one negative control group, NIH3T3 cells transferred with only MT5 vector were transplanted.

Figure 6:
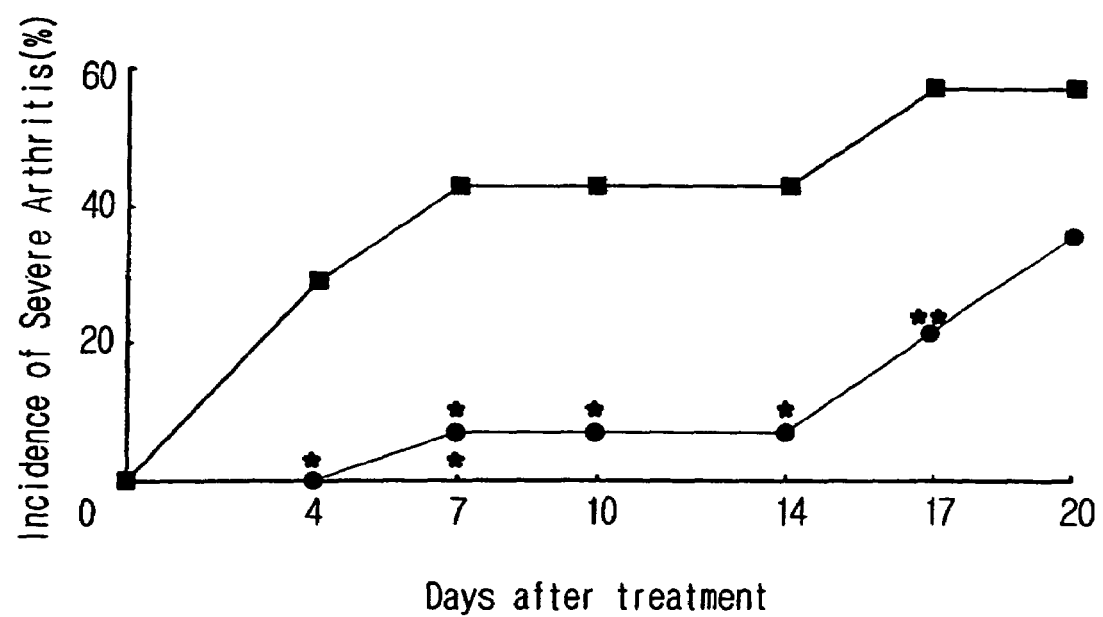
FIG. 6 is a graph showing the measurement results on duration of therapeutic effects of angiostatin-expressing NIH3T3 cells.

The incidence of serious-grade arthritis in feet (as the assessment criteria of ankle joint swelling is 3 or more) was measured on every third or fourth day from the transplant day to the $20^{th}$ day. As shown in FIG. 6, the result showed that the occurrence of serious-grade arthritis was inhibited up to the $14^{th}$ day after transplantation ($P<0.05$). This means that the therapeutic effect can be maintained for 14 days after treatment with one injection.

INDUSTRIAL APPLICABILITY

The gene therapy for treating rheumatoid arthritis using the genes encoding anti-angiogenic factors provided by the present invention can significantly inhibit the progress of arthritis not only in the macroscopic sign such as joint swelling, but also immunological and histological signs such as inflammation-associated cytokine level, synovial cell hyperplasia, and destruction of cartilage tissue. Accordingly, the present invention can be used to treat arthritis effectively in the situation that no effective treatment has been suggested for arthritis up to now.

---

What is claimed is:

1. A method of delaying the progression of one or more rheumatoid arthritis-associated symptoms in a patient having rheumatoid arthritis,
    wherein said symptoms are selected from the group consisting of: (i) joint swelling, (ii) synovial hyperplasia, (iii) cartilage destruction, and (iv) joint inflammation-associated cytokine level;
    said method comprising directly injecting into one or more sites of rheumatoid arthritis or sites adjacent thereto within the same limb of the patient a sufficient amount of a composition comprising:
        (a) a host cell comprising a nucleic acid encoding angiostatin or an anti-angiogenic fragment thereof, wherein said fragment comprises kringle structures 1 through 3 of plasminogen, and wherein said nucleic acid is operably linked to a signal sequence encoding a secretion peptide; and
        (b) a carrier,
    wherein said host cell is transformed by a retroviral vector comprising said nucleic acid operably linked to said signal sequence, and wherein said host cell is histocompatible with said patient.

2. The method of claim 1, wherein said retroviral vector is derived from the MT5 plasmid (KCCM Deposit No. 10205).

3. The method of claim 1, wherein said nucleic acid comprises a nucleotide sequence encoding amino acids 93–368 of SEQ ID NO:2.

4. The method of claim 1, wherein said nucleic acid comprises a nucleotide sequence encoding amino acids 93–440 of SEQ ID NO:2.

5. The method of claim 1, wherein said signal sequence encodes amino acids 1–18 of SEQ ID NO:2.

6. The method of claim 1, wherein said signal sequence comprises SEQ ID NO:13.

7. The method of claim 1, wherein said composition is injected into a site within the same limb as and adjacent to a site of rheumatoid arthritis.

8. The method of claim 7, wherein said composition is injected into a knee of said patient.

9. The method of claim 8, wherein the progression of joint swelling in an ankle of said patient is delayed.

* * * * *